(12) United States Patent
Murgita

(10) Patent No.: US 6,331,611 B1
(45) Date of Patent: *Dec. 18, 2001

(54) EXPRESSION AND PURIFICATION OF CLONED HUMAN ALPHA-FETOPROTEIN

(75) Inventor: Robert A. Murgita, Montreal (CA)

(73) Assignee: McGill University, Quebec (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/505,012

(22) Filed: Jul. 21, 1995

Related U.S. Application Data

(63) Continuation-in-part of application No. 08/377,317, filed on Jan. 24, 1995, now abandoned, which is a continuation-in-part of application No. 08/133,773, filed on Oct. 8, 1993, now Pat. No. 5,384,250, which is a continuation of application No. 07/767,435, filed on Sep. 27, 1991, now abandoned.

(51) Int. Cl.$^7$ .................................................. C07K 14/00
(52) U.S. Cl. ............................................ 530/350; 530/380
(58) Field of Search ................................ 530/350, 380; 435/69.6, 69.1

(56) References Cited

U.S. PATENT DOCUMENTS

| | | |
|---|---|---|
| 4,692,332 | 9/1987 | McMichael . |
| 4,745,051 | 5/1988 | Smith et al. . |
| 4,877,610 | 10/1989 | McMichael . |
| 4,966,753 | 10/1990 | McMichael . |
| 4,970,071 | 11/1990 | McMichael . |
| 5,011,844 | 4/1991 | Fehr . |
| 5,130,415 | 7/1992 | Tecce et al. . |
| 5,206,153 | 4/1993 | Tamaoki et al. . |
| 5,342,625 | 8/1994 | Hauer et al. . |
| 5,384,250 | * 1/1995 | Murgita .............................. 435/69.6 |

FOREIGN PATENT DOCUMENTS

| | | |
|---|---|---|
| 0 001 812 | 5/1979 | (EP) . |
| 20058666 | 1/1990 | (JP) . |
| WO 86/04241 | 7/1986 | (WO) . |
| WO 93/05774 | 4/1993 | (WO) . |
| WO 94/10199 | 5/1994 | (WO) . |

OTHER PUBLICATIONS

Nishi et al., J. Biochem. 104: 968–972 (1988).*
Boismenu et al., Life Sciences 43: 673–681 (1988).*
Moringa et al., PNAS 80 :4604–4606 (1983).*
Benjamin et al., Nature 320:449–451, 1986.
Hoskin et al., Cellular Immunology 96:163–174, 1985.
Murgita et al., Clin. Exp. Immunol. 33:347–356, 1978.

Abramsky, et al., Journal of Neuroimmunology, 2:1–7 (1982).

Abramsky et al., Annals New York Academy of Sciences, pp. 108–115 (1983).

Aoyagi et al., Gann, 75:809–815 (1984).

Biddle et al., Breast Cancer Research and Treatment, 10:279–286 (1897).

Boismenu et al., Life Sciences, 43:673–681 (1988).

Brenner et al., Annals New York Academy of Sciences, pp. 208–221.

Brenner et al., Proc. Natl. Acad. Sci. USA, 77:3635–3639 (1980).

Brenner et al., Immunology Letters, 3:163–167 (1981).

Buamah et al., Clinica Chimica Aca., 139:313–316 (1984).

Buschman et al., Journal of Neuroimmunology 13:315–330 (1987).

Cohen et al., Scand. J. Immunol. 23:211–223 (1986).

Dattwyler et al., Nature, 256:656–657 (1975).

Gershwin et al., The Journal of Immunology, 121:2292–2298 (1978).

Glazier et al., J. Exp. Med., 158:1–8 (1983).

Goidl et al., Development of Immunobiology, pp. 35–55 (1979).

Hamel et al., Phenotype and Function of Bone Marrow–Derived T–and Non–T–Cells Activated In Vitro By Alpha–Fetoprotein, In: Biological Activities of Alpha$_1$–Fetoprotein (vol. I), Mizejewski, G.J. and Jacobson, H.I (eds.), CRC Press, Inc. (Boca Raton, FL), pp. 167–177 (1987).

Heyward et al., The Lancet, pp. 1161–1162 (1983).

Hooper et al., Human AFP Inhibits Cell Proliferation and NK–Like Cytotoxic Activity Generated in Autologous, But Not In Allogeneic Mixed Lymphocyte Reactions, In: Biological Activities of Alpha$_1$–Fetoprotein, (vol. II) Mizejewski, G.J. and Jacobson, H.I (eds.), CRC Press, Inc. (Boca Raton, FL), pp. 183–197 (1989).

Hooper et al., Selective Inhibition Of Murine T–Cell Proliferation And Lymphokine–Activated Natural Killer Cell Function By alpha–Fetoprotein, In: Biological Activities of Alpha$_1$–Fetoprotein, (vol. I) Mizejewski, G.J. and Jacobson, H.I (eds.), CRC Press, Inc. (Boca Raton, FL), pp. 153–165 (1987).

(List continued on next page.)

Primary Examiner—Ethan Whisenant
(74) Attorney, Agent, or Firm—Clark & Elbing LLP

(57) ABSTRACT

Disclosed is substantially pure recombinant human alpha-fetoprotein produced using prokayote and insect cells.

19 Claims, 14 Drawing Sheets

OTHER PUBLICATIONS

Figure 2:
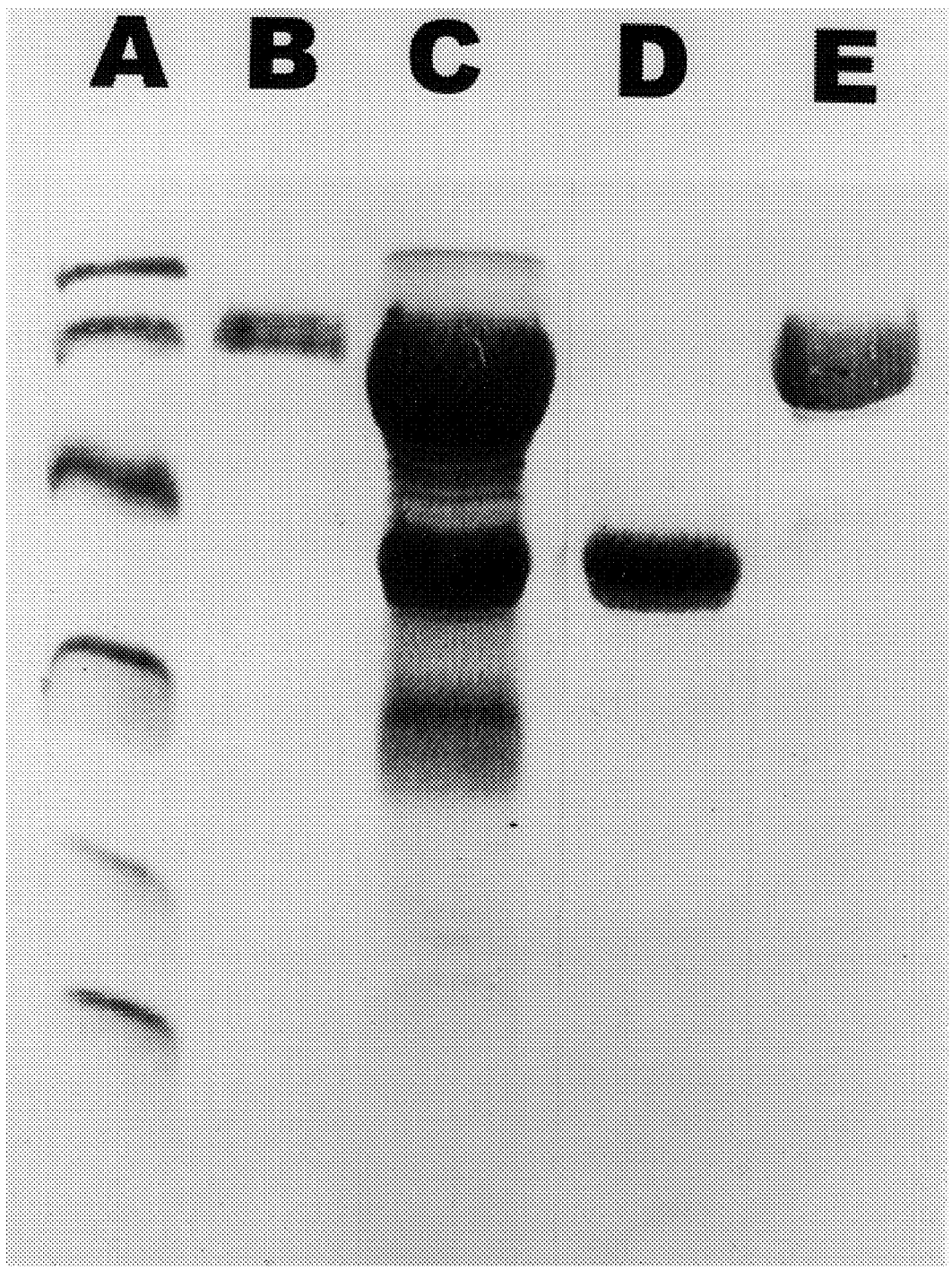

Hooper et al., Cellular Immunology, 63:417–425, (1981).
Hooper et al., Oncodevelopmental Biology and Medicine, 3:151–160 (1982).
Hoskin et al., Cellular Immunology, 96:163–174 (1985).
Hoskin et al., Clin. exp. Immunol., 76:262–267 (1989).
Hoskin et al., Analysis Of Pregnancy–Associated Immunoregulatory Pathways, In: Alpha–Fetoprotein and Congenital Disorders, Academic Press, New York, pp. 59–78, (1985).
Innis et al., Archives of Biochemistry and Biophysics, 195:128–135 (1979).
Ishiguro et al., Cancer, 55:156–159 (1985).
Jacobson et al., Cancer Research, 50:415–420 (1990).
Jiang et al., Science, 256:1213–1215 (1992).
Keller et al., Immunosuppressive Properties of AFP: Role of Estrogens, In: Onco–Developmental Gene Expression, Fishman, W.H. and Sell, S. (eds.), Academic Press, Inc. (New York) pp. 287–295 (1976).
Kikutani et al., Advances in Immunology, 51:285–322 (1992).
Line et al., Medical Potential Of AFP As A Tumor Imaging Agent, In: Biological Activites of Alpha$_1$–Fetoprotein (vol. II), Mizejewski, G.J. and Jacobson, H.I (eds.), CRC Press, Inc. (Boca Raton, FL), pp. 139–148 (1989).
Lu et al., The Journal of Immunology, 132:1722–1727 (1984).
Masuda et al., Tumor Biol., 15:175–183 (1994).
Mizejewski, Gerald J., Laboratory Management, (1987).
Morinaga et al., Proc. Natl. Acad. Sci. USA, 80:4604–4608 (1983).
Moro et al., Tumor Biol., 14:116–130 (1993).
Murgita et al., La Ricerca Clin. Lab., 9:327–342 (1979).
Murgita et al., Prog. Allergy, 29:54–133 (1981).
Murgita et al., The Journal of Experimental Medicine, 141:440–452 (1975).
Murgita et al., The Journal of Experimental Medicine, 141:269–286 (1975).
Murgita et al., Proc. Natl. Acad. Sci. USA, 75:2897–2901 (1978).
Murgita et al., Clin. exp. Immunol., 33:347–256 (1978).
Murgita et al., Scand. J. Immunol., 5:1215–1220 (1976).
Murgita, Scand. J. Immunol., 5:1003–1014 (1976).
Murgita et al., Nature, 267:257–259 (1977).
Murgita et al., Eur. J. Immunol., 11:957–964 (1981).
Nelson et al., The New England Journal of Medicine, 329:466–471 (1993).
Nishi et al., J. Biochem., 104:968–972 (1988).
O'Neill et al., Oncodevelopmental Biology and Medicine, 3:135–150 (1982).
Peck et al., The Journal of Immunology, 128:1134–1140 (1982).
Peck et al., The Journal of Experimental Medicine, 147:667–683 (1978).
Peck et al., J. Exp. Med., pp. 360–372.
Sell, S., In: Cancer Markers Diagnostic and Developmental Significance, Sell, S., (eds.), Humana Press, Clifton, NJ pp. 249–293 (1980).
Semeniuk et al., Abstract 2799, Experimental Biology 94™, Anaheim, CA (1994).
Soto et al., Proc. Natl. Acad. Sci. USA, 77:2084–2087 (1980).
van Oers et al., Journal of Chromatography, 525:59–69 (1990).
van Oers, et al., J. Exp. Med., 170:811–825 (1989).
Villacampa et al., Biochemical and Biophysical Research Communications, 122:1322–1327 (1984).
Yamamoto et al., Life Sciences, 46:1679–1686 (1990).
Giuliani et al., Protein Engineering, 2:605–610 (1989).
In: Baculovirus and Recombinant Proten Production Processes, eds., J.M. Viak, E.–J. Schlaeger, A.R. Bernard, Editiones Roche, Basel, Switzerland. pp. 67–73.

* cited by examiner

ATTGTGCTTCCACTGCCAATAACAAAATAACTAGCAACC

```
  1                                              10
thr leu his arg asn glu tyr gly ile ala
ACA CTG CAT AGA AAT GAA TAT GGA ATA GCT 31                                              40
phe phe ala gln phe val gln glu ala thr
TTT TTT GCC CAG TTT GTT CAA GAA GCC ACT 61                                              70
asp glu gln ser ser gly cys leu glu asn
GAT GAA CAG TCT TCA GGG TGT TTA GAA AAC 91                                             100
his ser asp cys cys ser gln ser glu glu
CAT TCA GAC TGC TGC AGC CAA AGT GAA GAG 121                                             130
gln val pro glu pro val thr ser cys glu
CAA GTT CCA GAA CCT GTC ACA AGC TGT GAA 151                                             160
his pro phe leu tyr ala pro thr ile leu
CAT CCC TTC CTG TAT GCA CCT ACA ATT CTT 181                                             190
glu cys phe gln thr lys ala ala thr val
GAA TGC TTC CAA ACA AAG GCA GCA ACA GTT 211                                             220
phe gly thr arg thr phe gln ala ile thr
TTT GGG ACC CGA ACT TTC CAA GCC ATA ACT 241                                             250
leu asp val ala his val his glu his cys
CTG GAT GTG GCC CAT GTA CAT GAG CAC TGT 271                                             280
ser gln gln asp thr leu ser asn lys ile
TCT CAA CAA GAC ACT CTG TCA AAC AAA ATA 301                                             310
asp glu lys pro glu gly leu ser pro asn
GAT GAA AAA CCT GAA GGT CTA TCT CCA AAT 331                                             340
phe leu ala ser phe val his glu tyr ser
TTC TTG GCA AGT TTT GTT CAT GAA TAT TCA
```

FIG. 1A

```
         -19
         met lys trp val glu ser ile phe leu
         ATG AAG TGG GTG GAA TCA ATT TTT TTA 20
ser ile leu asp ser tyr gln cys thr ala
TCC ATA TTG GAT TCT TAC CAA TGT ACT GCA 50
tyr lys glu val ser lys met val lys asp
TAC AAG GAA GTA AGC AAA ATG GTG AAA GAT 80
gln leu pro ala phe leu glu glu leu cys
CAG CTA CCT GCC TTT CTG GAA GAA CTT TGC 110
gly arg his asn cys phe leu ala his lys
GGA AGA CAT AAC TGT TTT CTT GCA CAC AAA 140
ala tyr glu glu asp arg glu thr phe met
GCA TAT GAA GAA GAC AGG GAG ACA TTC ATG 170
leu trp ala ala arg tyr asp lys ile ile
CTT TGG GCT GCT CGC TAT GAC AAA ATA ATT 200
thr lys glu leu arg glu ser ser leu leu
ACA AAA GAA TTA AGA GAA AGC AGC TTG TTA 230
val thr lys leu ser gln lys phe thr lys
GTT ACT AAA CTG AGT CAG AAG TTT ACC AAA 260
cys arg gly asp val leu asp cys leu gln
TGC AGA GGA GAT GTG CTG GAT TGT CTG CAG 290
thr glu cys cys lys leu thr thr leu glu
ACA GAA TGC TGC AAA CTG ACC ACG CTG GAA 320
leu asn arg phe leu gly asp arg asp phe
CTA AAC AGG TTT TTA GGA GAT AGA GAT TTT 350
arg arg his pro gln leu ala val ser val
AGA AGA CAT CCT CAG CTT GCT GTC TCA GTA
```

FIG. 1B

```
                                                            AT    (2)
      -10                                              -1
      ile phe leu leu asn phe thr glu ser arg
      ATT TTC CTA CTA AAT TTT ACT GAA TCC AGA         (101)

30
      glu ile ser leu ala asp leu ala thr ile
      GAG ATA AGT TTA GCT GAC CTG GCT ACC ATA         (191)

60
      ala leu thr ala ile glu lys pro thr gly
      GCA TTG ACT GCA ATT GAG AAA CCC ACT GGA         (281)

90
      his glu lys glu ile leu glu lys tyr gly
      CAT GAG AAA GAA ATT TTG GAG AAG TAC GGA         (371)

120
      lys pro thr pro ala ser ile pro leu phe
      AAG CCC ACT CCA GCA TCG ATC CCA CTT TTC         (461)

150
      asn lys phe ile tyr glu ile ala arg arg
      AAC AAA TTC ATT TAT GAG ATA GCA AGA AGG         (551)

180
      pro ser cys cys lys ala glu asn ala val
      CCA TCT TGC TGC AAA GCT GAA AAT GCA GTT         (641)

210
      asn gln his ala cys ala val met lys asn
      AAT CAA CAT GCA TGT GCA GTA ATG AAA AAT         (731)

240
      val asn phe thr glu ile gln lys leu val
      GTT AAT TTT ACT GAA ATC CAG AAA CTA GTC         (821)

270
      asp gly glu lys ile met ser tyr ile cys
      GAT GGG GAA AAA ATC ATG TCC TAC ATA TGT         (911)

300
      arg gly gln cys ile ile his ala glu asn
      CGT GGT CAA TGT ATA ATT CAT GCA GAA AAT        (1001)

330
      asn gln phe ser ser gly glu lys asn ile
      AAC CAA TTT TCT TCA GGG GAA AAA AAT ATC        (1091)

360
      ile leu arg val ala lys gly tyr gln glu
      ATT CTA AGA GTT GCT AAA GGA TAC CAG GAG        (1181)
```

FIG. 1C

```
361                                              370
leu leu glu lys cys phe gln thr glu asn
TTA TTG GAG AAG TGT TTC CAG ACT GAA AAC 391                                              400
ala leu ala lys arg ser cys gly leu phe
GCA TTG GCA AAG CGA AGC TGC GGC CTC TTC 421                                              430
pro gln leu thr ser ser glu leu met ala
CCC CAG CTG ACC TCG TCG GAG CTG ATG GCC 451                                              460
leu ala cys gly glu gly ala ala asp ile
TTG GCC TGT GGC GAG GGA GCG GCT GAC ATT 481                                              490
cys cys thr ser ser tyr ala asn arg arg
TGC TGC ACT TCT TCA TAT GCC AAC AGG AGG 511                                              520
lys phe ile phe his lys asp leu cys gln
AAG TTC ATT TTC CAT AAG GAT CTG TGC CAA 541                                              550
lys pro gln ile thr glu glu gln leu glu
AAG CCA CAA ATA ACA GAG GAA CAA CTT GAG 571                                              580
val cys phe ala glu glu gly gln lys leu
GTC TGC TTT GCT GAA GAG GGA CAA AAA CTG
```

TTCATTCGGTGTGAACTTTTCTCTTTAATTTTAACTGA

TG(A) 10 (2039)

FIG. 1D

```
                                              380
pro leu glu cys gln asp lys gly glu glu
CCT CTT GAA TGC CAA GAT AAA GGA GAA GAA 410
gln lys leu gly glu tyr tyr leu gln asn
CAG AAA CTA GGA GAA TAT TAC TTA CAA AAT 440
ile thr arg lys met ala ala thr ala ala
ATC ACC AGA AAA ATG GCA GCC ACA GCA GCC 470
ile ile gly his leu cys ile arg his glu
ATT ATC GGA CAC TTA TGT ATC AGA CAT GAA 500
pro cys phe ser ser leu val val asp glu
CCA TGC TTC AGC AGC TTG GTG GTG GAT GAA 530
ala gln gly val ala leu gln thr met lys
GCT CAG GGT GTA GCG CTG CAA ACG ATG AAG 560
ala val ile ala asp phe ser gly leu leu
GCT GTC ATT GCA GAT TTC TCA GGC CTG TTG 590
ile ser lys thr arg ala ala leu gly val
ATT TCA AAA ACT CGT GCT GCT TTG GGA GTT
```

TTTAACACTTTTTGTGAATTAATGAAATGATAAAGACTTTTA

FIG. 1E

```
                                                390
glu leu gln lys tyr ile gln glu ser gln
GAA TTA CAG AAA TAC ATC CAG GAG AGC CAA (1271)

420
ala phe leu val ala tyr thr lys lys ala
GCG TTT CTC GTT GCT TAC ACA AAG AAA GCC (1361)

450
thr cys cys gln leu ser glu asp lys leu
ACT TGT TGC CAA CTC AGT GAG GAC AAA CTA (1451)

480
met thr pro val asn pro gly val gly gln
ATG ACT CCA GTA AAC CCT GGT GTT GGC CAG (1541)

510
thr tyr val pro pro ala phe ser asp asp
ACA TAT GTC CCT CCT GCA TTC TCT GAT GAC (1631)

540
gln glu phe leu ile asn leu val lys gln
CAA GAG TTT CTC ATT AAC CTT GTG AAG CAA (1721)

570
glu lys cys cys gln gly gln glu gln glu
GAG AAA TGC TGC CAA GGC CAG GAA CAG GAA (1811)

ter
TAA    ATTACTTCAGGGGAAGAGAAGACAAAACGAGTCT (1908)

TGTGAGATTTCCTTATCACAGAAATAAAATATCTCCAAA (2027)
```

FIG. 1F

| FIG. 1A | FIG. 1B | FIG. 1C |
|---------|---------|---------|
| FIG. 1D | FIG. 1E | FIG. 1F |

FIG. 1G

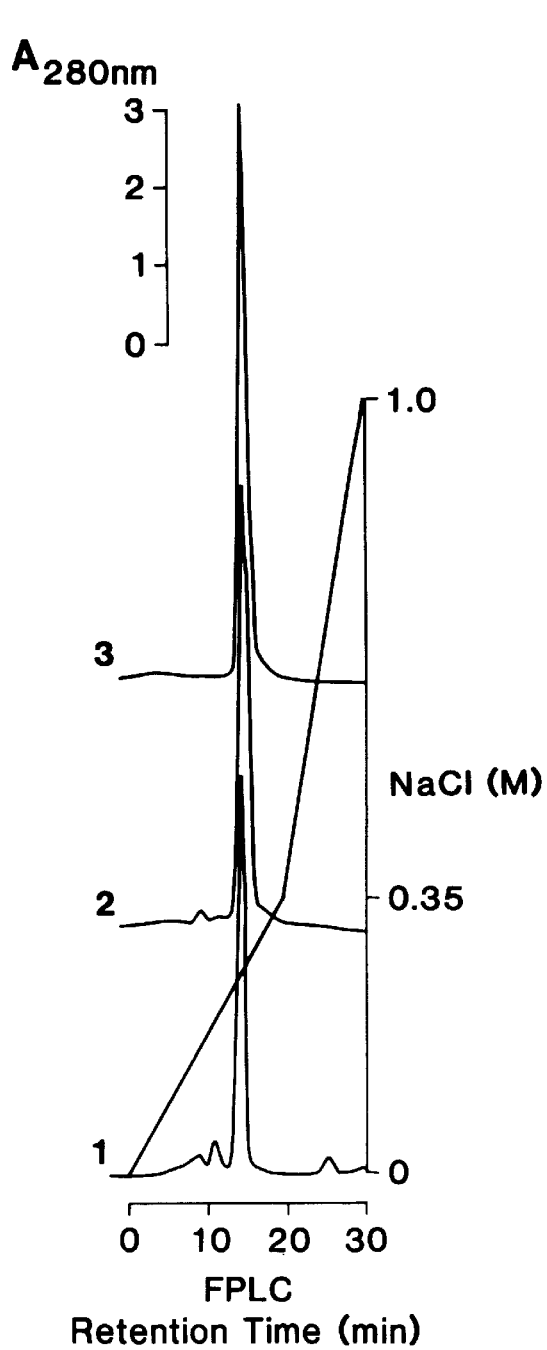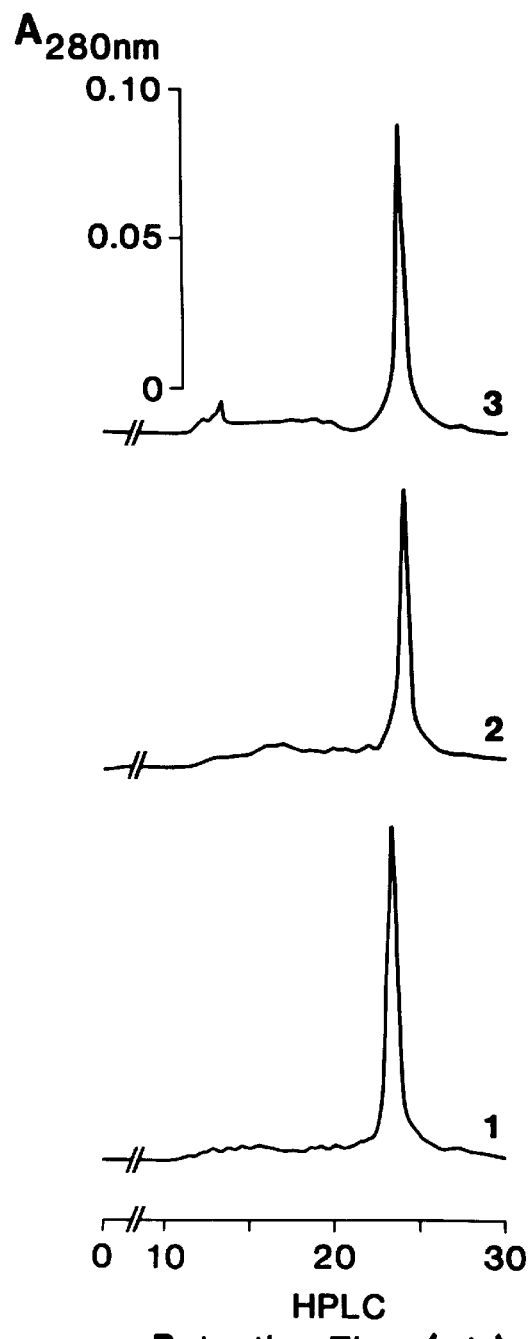
FIG. 4C
FIG. 4D

```
                          SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:1:

TGTCTGCAGG ATGGGGAAAA A                                          21

(2) INFORMATION FOR SEQ ID NO:2:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:2:

CATGAAATGA CTCCAGTA                                              18

(2) INFORMATION FOR SEQ ID NO:3:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:3:

CATAGAAATG AATATGGA                                              18

(2) INFORMATION FOR SEQ ID NO:4:

(i) SEQUENCE CHARACTERISTICS:
             (A) LENGTH: 2022 base pairs
             (B) TYPE: nucleic acid
             (C) STRANDEDNESS: Not Relevant
             (D) TOPOLOGY: linear (ii) MOLECULE TYPE:

(xi) SEQUENCE DESCRIPTION: SEQ ID NO:4:

ATATTGTGCT TCCACCACTG CCAATAACAA AATAACTAGC AACCATGAAG TGGGTGGAAT    60
```

-continued

```
CAATTTTTTT AATTTTCCTA CTAAATTTTA CTGAATCCAG AACACTGCAT AGAAATGAAT    120

ATGGAATAGC TTCCATATTG GATTCTTACC AATGTACTGC AGAGATAAGT TTAGCTGACC    180

TGGCTACCAT ATTTTTTGCC CAGTTTGTTC AAGAAGCCAC TTACAAGGAA GTAAGCAAAA    240

TGGTGAAAGA TGCATTGACT GCAATTGAGA AACCCACTGG AGATGAACAG TCTTCAGGGT    300

GTTTAGAAAA CCAGCTACCT GCCTTTCTGG AAGAACTTTG CCATGAGAAA GAAATTTTGG    360

AGAAGTACGG ACATTCAGAC TGCTGCAGCC AAAGTGAAGA GGGAAGACAT AACTGTTTTC    420

TTGCACACAA AAAGCCCACT GCAGCATGGA TCCCACTTTT CCAAGTTCCA GAACCTGTCA    480

CAAGCTGTGA AGCATATGAA GAAGACAGGG AGACATTCAT GAACAAATTC ATTTATGAGA    540

TAGCAAGAAG GCATCCCTTC CTGTATGCAC CTACAATTCT TCTTTCGGCT GCTGGGTATG    600

AGAAAATAAT TCCATCTTGC TGCAAAGCTG AAAATGCAGT TGAATGCTTC CAAACAAAGG    660

CAGCAACAGT TACAAAAGAA TTAAGAGAAA GCAGCTTGTT AAATCAACAT GCATGTCCAG    720

TAATGAAAAA TTTTGGGACC CGAACTTTCC AAGCCATAAC TGTTACTAAA CTGAGTCAGA    780

AGTTTACCAA AGTTAATTTT ACTGAAATCC AGAAACTAGT CCTGGATGTG GCCCATGTAC    840

ATGAGCACTG TTGCAGAGCA GATGTGCTGG ATTGTCTGCA GGATGGGGAA AAAATCATGT    900

CCTACATATG TTCTCAACAA GACACTCTGT CAAACAAAAT AACAGAATGC TGCAAACTGA    960

CCACGCTGGA ACGTGGTCAA TGTATAATTC ATGCAGAAAA TGATGAAAAA CCTGAAGGTC   1020

TATCTCCAAA TCTAAACAGG TTTTTAGGAG ATAGAGATTT TAACCAATTT TCTTCAGGGG   1080

AAAAAAATAT CTTCTTGGCA AGTTTTGTTC ATGAATATTC AAGAAGACAT CCTCAGCTTG   1140

CTGTCTCAGT AATTCTAAGA GTTGCTAAAG GATACCAGGA GTTATTGGAG AAGTGTTTCC   1200

AGACTGAAAA CCCTCTTGAA TGCCAAGATA AGGAGAAGA AGAATTACAG AAATACATCC   1260

AGGAGAGCCA AGCATTGGCA AAGCGAAGCT GCGGCCTCTT CCAGAAACTA GGAGAATATT   1320

ACTTACAAAA TGAGTTTCTC GTTGCTTACA CAAAGAAAGC CCCCCAGCTG ACCTCGTCGG   1380

AGCTGATGGC CATCACCAGA AAAATGGCAG CCACAGCAGC CACTTGTTGC CAACTCAGTG   1440

AGGACAAACT ATTGGCCTGT GGCGAGGGAG CGGCTGACAT TATTATCGGA CACTTATGTA   1500

TCAGACATGA AATGACTCCA GTAAACCCTG GTGTTGGCCA GTGCTGCACT TCTTCATATG   1560

CCAACAGGAG GCCATGCTTC AGCAGCTTGG TGGTGGATGA ACATATGTC CCTCCTGCAT    1620

TCTCTGATGA CAAGTTCATT TTCCATAAGG ATCTGTGCCA AGCTCAGGGT GTAGCGCTGC   1680

AAAGGATGAA GCAAGAGTTT CTCATTAACC TTGTGAAGCA AAAGCCACAA ATAACAGAGG   1740

AACAACTTGA GGCTCTCATT GCAGATTTCT CAGGCCTGTT GGAGAAATGC TGCCAAGGCC   1800

AGGAACAGGA AGTCTGCTTT GCTGAAGAGG GACAAAAACT GATTTCAAAA ACTGGTGCTG   1860

CTTTGGGAGT TTAAATTACT TCAGGGGAAG AGAAGACAAA ACGAGTCTTT CATTCGGTGT   1920

GAACTTTTCT CTTTAATTTT AACTGATTTA ACACTTTTTG TGAATTAATG ATAAAGACTT   1980

TTATGTGAGA TTTCCTTATC ACAGAAATAA AATATCTCCA AA                      2022
```

(2) INFORMATION FOR SEQ ID NO:5:

(i) SEQUENCE CHARACTERISTICS:
        (A) LENGTH: 590 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:5:

-continued

```
Thr Leu His Arg Asn Glu Tyr Gly Ile Ala Ser Ile Leu Asp Ser Tyr
1               5                   10                  15

Gln Cys Thr Ala Glu Ile Ser Leu Ala Asp Leu Ala Thr Ile Phe Phe
            20                  25                  30

Ala Gln Phe Val Gln Glu Ala Thr Tyr Lys Glu Val Ser Lys Met Val
            35                  40                  45

Lys Asp Ala Leu Thr Ala Ile Glu Lys Pro Thr Gly Asp Glu Gln Ser
50                  55                  60

Ser Gly Cys Leu Glu Asn Gln Leu Pro Ala Phe Leu Glu Glu Leu Cys
65                  70                  75                  80

His Glu Lys Glu Ile Leu Glu Lys Tyr Gly His Ser Asp Cys Cys Ser
                85                  90                  95

Gln Ser Glu Glu Gly Arg His Asn Cys Phe Leu Ala His Lys Lys Pro
            100                 105                 110

Thr Ala Ala Trp Ile Pro Leu Phe Gln Val Pro Glu Pro Val Thr Ser
            115                 120                 125

Cys Glu Ala Tyr Glu Glu Asp Arg Glu Thr Phe Met Asn Lys Phe Ile
130                 135                 140

Tyr Glu Ile Ala Arg Arg His Pro Phe Leu Tyr Ala Pro Thr Ile Leu
145                 150                 155                 160

Leu Ser Ala Ala Gly Tyr Glu Lys Ile Ile Pro Ser Cys Cys Lys Ala
                165                 170                 175

Glu Asn Ala Val Glu Cys Phe Gln Thr Lys Ala Ala Thr Val Thr Lys
            180                 185                 190

Glu Leu Arg Glu Ser Ser Leu Leu Asn Gln His Ala Cys Pro Val Met
            195                 200                 205

Lys Asn Phe Gly Thr Arg Thr Phe Gln Ala Ile Thr Val Thr Lys Leu
            210                 215                 220

Ser Gln Lys Phe Thr Lys Val Asn Phe Thr Glu Ile Gln Lys Leu Val
225                 230                 235                 240

Leu Asp Val Ala His Val His Glu His Cys Cys Arg Ala Asp Val Leu
                245                 250                 255

Asp Cys Leu Gln Asp Gly Glu Lys Ile Met Ser Tyr Ile Cys Ser Gln
            260                 265                 270

Gln Asp Thr Leu Ser Asn Lys Ile Thr Glu Cys Cys Lys Leu Thr Thr
            275                 280                 285

Leu Glu Arg Gly Gln Cys Ile Ile His Ala Glu Asn Asp Glu Lys Pro
290                 295                 300

Glu Gly Leu Ser Pro Asn Leu Asn Arg Phe Leu Gly Asp Arg Asp Phe
305                 310                 315                 320

Asn Gln Phe Ser Ser Gly Glu Lys Asn Ile Phe Leu Ala Ser Phe Val
                325                 330                 335

His Glu Tyr Ser Arg Arg His Pro Gln Leu Ala Val Ser Val Ile Leu
            340                 345                 350

Arg Val Ala Lys Gly Tyr Gln Glu Leu Leu Glu Lys Cys Phe Gln Thr
            355                 360                 365

Glu Asn Pro Leu Glu Cys Gln Asp Lys Gly Glu Glu Glu Leu Gln Lys
370                 375                 380

Tyr Ile Gln Glu Ser Gln Ala Leu Ala Lys Arg Ser Cys Gly Leu Phe
385                 390                 395                 400

Gln Lys Leu Gly Glu Tyr Tyr Leu Gln Asn Glu Phe Leu Val Ala Tyr
                405                 410                 415

Thr Lys Lys Ala Pro Gln Leu Thr Ser Ser Glu Leu Met Ala Ile Thr
```

|                        | 420 |                        | 425 |                        | 430 |
|---|---|---|---|---|---|

Arg Lys Met Ala Ala Thr Ala Ala Thr Cys Cys Gln Leu Ser Glu Asp
      435                    440                    445

Lys Leu Leu Ala Cys Gly Glu Gly Ala Ala Asp Ile Ile Ile Gly His
450                    455                    460

Leu Cys Ile Arg His Glu Met Thr Pro Val Asn Pro Gly Val Gly Gln
465                    470                    475                    480

Cys Cys Thr Ser Ser Tyr Ala Asn Arg Arg Pro Cys Phe Ser Ser Leu
                485                    490                    495

Val Val Asp Glu Thr Tyr Val Pro Pro Ala Phe Ser Asp Asp Lys Phe
              500                    505                    510

Ile Phe His Lys Asp Leu Cys Gln Ala Gln Gly Val Ala Leu Gln Arg
      515                    520                    525

Met Lys Gln Glu Phe Leu Ile Asn Leu Val Lys Gln Lys Pro Gln Ile
530                    535                    540

Thr Glu Glu Gln Leu Glu Ala Leu Ile Ala Asp Phe Ser Gly Leu Leu
545                    550                    555                    560

Glu Lys Cys Cys Gln Gly Gln Glu Gln Glu Val Cys Phe Ala Glu Glu
                565                    570                    575

Gly Gln Lys Leu Ile Ser Lys Thr Gly Ala Ala Leu Gly Val
              580                    585                    590

(2) INFORMATION FOR SEQ ID NO:6:

(i) SEQUENCE CHARACTERISTICS:
        (A) LENGTH: 197 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:6:

Thr Leu His Arg Asn Glu Tyr Gly Ile Ala Ser Ile Leu Asp Ser Tyr
1                5                    10                    15

Gln Cys Thr Ala Glu Ile Ser Leu Ala Asp Leu Ala Thr Ile Phe Phe
                20                    25                    30

Ala Gln Phe Val Gln Glu Ala Thr Tyr Lys Glu Val Ser Lys Met Val
              35                    40                    45

Lys Asp Ala Leu Thr Ala Ile Glu Lys Pro Thr Gly Asp Glu Gln Ser
50                    55                    60

Ser Gly Cys Leu Glu Asn Gln Leu Pro Ala Phe Leu Glu Glu Leu Cys
65                    70                    75                    80

His Glu Lys Glu Ile Leu Glu Lys Tyr Gly His Ser Asp Cys Cys Ser
                85                    90                    95

Gln Ser Glu Glu Gly Arg His Asn Cys Phe Leu Ala His Lys Lys Pro
              100                    105                    110

Thr Ala Ala Trp Ile Pro Leu Phe Gln Val Pro Glu Pro Val Thr Ser
              115                    120                    125

Cys Glu Ala Tyr Glu Glu Asp Arg Glu Thr Phe Met Asn Lys Phe Ile
              130                    135                    140

Tyr Glu Ile Ala Arg Arg His Pro Phe Leu Tyr Ala Pro Thr Ile Leu
145                    150                    155                    160

Leu Ser Ala Ala Gly Tyr Glu Lys Ile Ile Pro Ser Cys Cys Lys Ala
              165                    170                    175

Glu Asn Ala Val Glu Cys Phe Gln Thr Lys Ala Ala Thr Val Thr Lys

-continued

```
                180                 185                 190
Glu Leu Arg Glu Ser
            195

(2) INFORMATION FOR SEQ ID NO:7:

(i) SEQUENCE CHARACTERISTICS:
        (A) LENGTH: 192 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:7:

Ser Leu Leu Asn Gln His Ala Cys Pro Val Met Lys Asn Phe Gly Thr
1               5                   10                  15

Arg Thr Phe Gln Ala Ile Thr Val Thr Lys Leu Ser Gln Lys Phe Thr
            20                  25                  30

Lys Val Asn Phe Thr Glu Ile Gln Lys Leu Val Leu Asp Val Ala His
            35                  40                  45

Val His Glu His Cys Cys Arg Ala Asp Val Leu Asp Cys Leu Gln Asp
        50                  55                  60

Gly Glu Lys Ile Met Ser Tyr Ile Cys Ser Gln Gln Asp Thr Leu Ser
65                  70                  75                  80

Asn Lys Ile Thr Glu Cys Cys Lys Leu Thr Thr Leu Glu Arg Gly Gln
                85                  90                  95

Cys Ile Ile His Ala Glu Asn Asp Glu Lys Pro Glu Gly Leu Ser Pro
                100                 105                 110

Asn Leu Asn Arg Phe Leu Gly Asp Arg Asp Phe Asn Gln Phe Ser Ser
            115                 120                 125

Gly Glu Lys Asn Ile Phe Leu Ala Ser Phe Val His Glu Tyr Ser Arg
        130                 135                 140

Arg His Pro Gln Leu Ala Val Ser Val Ile Leu Arg Val Ala Lys Gly
145                 150                 155                 160

Tyr Gln Glu Leu Leu Glu Lys Cys Phe Gln Thr Glu Asn Pro Leu Glu
                165                 170                 175

Cys Gln Asp Lys Gly Glu Glu Leu Gln Lys Tyr Ile Gln Glu Ser
            180                 185                 190

(2) INFORMATION FOR SEQ ID NO:8:

(i) SEQUENCE CHARACTERISTICS:
        (A) LENGTH: 201 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:8:

Gln Ala Leu Ala Lys Arg Ser Cys Gly Leu Phe Gln Lys Leu Gly Glu
1               5                   10                  15

Tyr Tyr Leu Gln Asn Glu Phe Leu Val Ala Tyr Thr Lys Lys Ala Pro
            20                  25                  30

Gln Leu Thr Ser Ser Glu Leu Met Ala Ile Thr Arg Lys Met Ala Ala
            35                  40                  45

Thr Ala Ala Thr Cys Cys Gln Leu Ser Glu Asp Lys Leu Leu Ala Cys
        50                  55                  60
```

```
Gly Glu Gly Ala Ala Asp Ile Ile Gly His Leu Cys Ile Arg His
 65                  70                  75                  80

Glu Met Thr Pro Val Asn Pro Gly Val Gly Gln Cys Cys Thr Ser Ser
                 85                  90                  95

Tyr Ala Asn Arg Arg Pro Cys Phe Ser Ser Leu Val Val Asp Glu Thr
            100                 105                 110

Tyr Val Pro Pro Ala Phe Ser Asp Asp Lys Phe Ile Phe His Lys Asp
        115                 120                 125

Leu Cys Gln Ala Gln Gly Val Ala Leu Gln Arg Met Lys Gln Glu Phe
130                 135                 140

Leu Ile Asn Leu Val Lys Gln Lys Pro Gln Ile Thr Glu Glu Gln Leu
145                 150                 155                 160

Glu Ala Leu Ile Ala Asp Phe Ser Gly Leu Leu Glu Lys Cys Cys Gln
                165                 170                 175

Gly Gln Glu Gln Glu Val Cys Phe Ala Glu Glu Gly Gln Lys Leu Ile
            180                 185                 190

Ser Lys Thr Gly Ala Ala Leu Gly Val
            195                 200
```

(2) INFORMATION FOR SEQ ID NO:9:

(i) SEQUENCE CHARACTERISTICS:
        (A) LENGTH: 389 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:9:

```
Thr Leu His Arg Asn Glu Tyr Gly Ile Ala Ser Ile Leu Asp Ser Tyr
  1               5                  10                  15

Gln Cys Thr Ala Glu Ile Ser Leu Ala Asp Leu Ala Thr Ile Phe Phe
             20                  25                  30

Ala Gln Phe Val Gln Glu Ala Thr Tyr Lys Glu Val Ser Lys Met Val
         35                  40                  45

Lys Asp Ala Leu Thr Ala Ile Glu Lys Pro Thr Gly Asp Glu Gln Ser
 50                  55                  60

Ser Gly Cys Leu Glu Asn Gln Leu Pro Ala Phe Leu Glu Glu Leu Cys
 65                  70                  75                  80

His Glu Lys Glu Ile Leu Glu Lys Tyr Gly His Ser Asp Cys Cys Ser
             85                  90                  95

Gln Ser Glu Glu Gly Arg His Asn Cys Phe Leu Ala His Lys Lys Pro
            100                 105                 110

Thr Ala Ala Trp Ile Pro Leu Phe Gln Val Pro Glu Pro Val Thr Ser
            115                 120                 125

Cys Glu Ala Tyr Glu Glu Asp Arg Glu Thr Phe Met Asn Lys Phe Ile
130                 135                 140

Tyr Glu Ile Ala Arg Arg His Pro Phe Leu Tyr Ala Pro Thr Ile Leu
145                 150                 155                 160

Leu Ser Ala Ala Gly Tyr Glu Lys Ile Ile Pro Ser Cys Cys Lys Ala
                165                 170                 175

Glu Asn Ala Val Glu Cys Phe Gln Thr Lys Ala Ala Thr Val Thr Lys
            180                 185                 190

Glu Leu Arg Glu Ser Ser Leu Leu Asn Gln His Ala Cys Pro Val Met
            195                 200                 205
```

```
Lys Asn Phe Gly Thr Arg Thr Phe Gln Ala Ile Thr Val Thr Lys Leu
    210                 215                 220

Ser Gln Lys Phe Thr Lys Val Asn Phe Thr Glu Ile Gln Lys Leu Val
225                 230                 235                 240

Leu Asp Val Ala His Val His Glu His Cys Cys Arg Ala Asp Val Leu
                245                 250                 255

Asp Cys Leu Gln Asp Gly Glu Lys Ile Met Ser Tyr Ile Cys Ser Gln
                260                 265                 270

Gln Asp Thr Leu Ser Asn Lys Ile Thr Glu Cys Cys Lys Leu Thr Thr
            275                 280                 285

Leu Glu Arg Gly Gln Cys Ile Ile His Ala Glu Asn Asp Glu Lys Pro
        290                 295                 300

Glu Gly Leu Ser Pro Asn Leu Asn Arg Phe Leu Gly Asp Arg Asp Phe
305                 310                 315                 320

Asn Gln Phe Ser Ser Gly Glu Lys Asn Ile Phe Leu Ala Ser Phe Val
                325                 330                 335

His Glu Tyr Ser Arg Arg His Pro Gln Leu Ala Val Ser Val Ile Leu
                340                 345                 350

Arg Val Ala Lys Gly Tyr Gln Glu Leu Leu Glu Lys Cys Phe Gln Thr
            355                 360                 365

Glu Asn Pro Leu Glu Cys Gln Asp Lys Gly Glu Glu Leu Gln Lys
        370                 375                 380

Tyr Ile Gln Glu Ser
385

(2) INFORMATION FOR SEQ ID NO:10:

(i) SEQUENCE CHARACTERISTICS:
        (A) LENGTH: 393 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:10:

Ser Leu Leu Asn Gln His Ala Cys Pro Val Met Lys Asn Phe Gly Thr
1               5                   10                  15

Arg Thr Phe Gln Ala Ile Thr Val Thr Lys Leu Ser Gln Lys Phe Thr
                20                  25                  30

Lys Val Asn Phe Thr Glu Ile Gln Lys Leu Val Leu Asp Val Ala His
            35                  40                  45

Val His Glu His Cys Cys Arg Ala Asp Val Leu Asp Cys Leu Gln Asp
50                  55                  60

Gly Glu Lys Ile Met Ser Tyr Ile Cys Ser Gln Gln Asp Thr Leu Ser
65                  70                  75                  80

Asn Lys Ile Thr Glu Cys Cys Lys Leu Thr Thr Leu Glu Arg Gly Gln
                85                  90                  95

Cys Ile Ile His Ala Glu Asn Asp Glu Lys Pro Glu Gly Leu Ser Pro
            100                 105                 110

Asn Leu Asn Arg Phe Leu Gly Asp Arg Asp Phe Asn Gln Phe Ser Ser
        115                 120                 125

Gly Glu Lys Asn Ile Phe Leu Ala Ser Phe Val His Glu Tyr Ser Arg
    130                 135                 140

Arg His Pro Gln Leu Ala Val Ser Val Ile Leu Arg Val Ala Lys Gly
145                 150                 155                 160
```

```
Tyr Gln Glu Leu Leu Glu Lys Cys Phe Gln Thr Glu Asn Pro Leu Glu
                165                 170                 175
Cys Gln Asp Lys Gly Glu Glu Leu Gln Lys Tyr Ile Gln Glu Ser
                180                 185                 190
Gln Ala Leu Ala Lys Arg Ser Cys Gly Leu Phe Gln Lys Leu Gly Glu
                195                 200                 205
Tyr Tyr Leu Gln Asn Glu Phe Leu Val Ala Tyr Thr Lys Lys Ala Pro
                210                 215                 220
Gln Leu Thr Ser Ser Glu Leu Met Ala Ile Thr Arg Lys Met Ala Ala
225                 230                 235                 240
Thr Ala Ala Thr Cys Cys Gln Leu Ser Glu Asp Lys Leu Leu Ala Cys
                245                 250                 255
Gly Glu Gly Ala Ala Asp Ile Ile Ile Gly His Leu Cys Ile Arg His
                260                 265                 270
Glu Met Thr Pro Val Asn Pro Gly Val Gly Gln Cys Cys Thr Ser Ser
                275                 280                 285
Tyr Ala Asn Arg Arg Pro Cys Phe Ser Ser Leu Val Val Asp Glu Thr
                290                 295                 300
Tyr Val Pro Pro Ala Phe Ser Asp Asp Lys Phe Ile Phe His Lys Asp
305                 310                 315                 320
Leu Cys Gln Ala Gln Gly Val Ala Leu Gln Arg Met Lys Gln Glu Phe
                325                 330                 335
Leu Ile Asn Leu Val Lys Gln Lys Pro Gln Ile Thr Glu Glu Gln Leu
                340                 345                 350
Glu Ala Leu Ile Ala Asp Phe Ser Gly Leu Leu Glu Lys Cys Cys Gln
                355                 360                 365
Gly Gln Glu Gln Glu Val Cys Phe Ala Glu Glu Gly Gln Lys Leu Ile
                370                 375                 380
Ser Lys Thr Gly Ala Ala Leu Gly Val
385                 390

(2) INFORMATION FOR SEQ ID NO:11:

(i) SEQUENCE CHARACTERISTICS:
        (A) LENGTH: 325 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:11:

Met Ser Tyr Ile Cys Ser Gln Gln Asp Thr Leu Ser Asn Lys Ile Thr
1               5                   10                  15
Glu Cys Cys Lys Leu Thr Thr Leu Glu Arg Gly Gln Cys Ile Ile His
                20                  25                  30
Ala Glu Asn Asp Glu Lys Pro Glu Gly Leu Ser Pro Asn Leu Asn Arg
                35                  40                  45
Phe Leu Gly Asp Arg Asp Phe Asn Gln Phe Ser Ser Gly Glu Lys Asn
                50                  55                  60
Ile Phe Leu Ala Ser Phe Val His Glu Tyr Ser Arg Arg His Pro Gln
65                  70                  75                  80
Leu Ala Val Ser Val Ile Leu Arg Val Ala Lys Gly Tyr Gln Glu Leu
                85                  90                  95
Leu Glu Lys Cys Phe Gln Thr Glu Asn Pro Leu Glu Cys Gln Asp Lys
                100                 105                 110
```

-continued

```
Gly Glu Glu Glu Leu Gln Lys Tyr Ile Gln Glu Ser Gln Ala Leu Ala
        115                 120                 125

Lys Arg Ser Cys Gly Leu Phe Gln Lys Leu Gly Glu Tyr Tyr Leu Gln
130                 135                 140

Asn Glu Phe Leu Val Ala Tyr Thr Lys Lys Ala Pro Gln Leu Thr Ser
145                 150                 155                 160

Ser Glu Leu Met Ala Ile Thr Arg Lys Met Ala Ala Thr Ala Ala Thr
            165                 170                 175

Cys Cys Gln Leu Ser Glu Asp Lys Leu Leu Ala Cys Gly Glu Gly Ala
                180                 185                 190

Ala Asp Ile Ile Ile Gly His Leu Cys Ile Arg His Glu Met Thr Pro
            195                 200                 205

Val Asn Pro Gly Val Gly Gln Cys Cys Thr Ser Ser Tyr Ala Asn Arg
        210                 215                 220

Arg Pro Cys Phe Ser Ser Leu Val Val Asp Glu Thr Tyr Val Pro Pro
225                 230                 235                 240

Ala Phe Ser Asp Asp Lys Phe Ile Phe His Lys Asp Leu Cys Gln Ala
                245                 250                 255

Gln Gly Val Ala Leu Gln Arg Met Lys Gln Glu Phe Leu Ile Asn Leu
            260                 265                 270

Val Lys Gln Lys Pro Gln Ile Thr Glu Glu Gln Leu Glu Ala Leu Ile
        275                 280                 285

Ala Asp Phe Ser Gly Leu Leu Glu Lys Cys Cys Gln Gly Gln Glu Gln
        290                 295                 300

Glu Val Cys Phe Ala Glu Glu Gly Gln Lys Leu Ile Ser Lys Thr Gly
305                 310                 315                 320

Ala Ala Leu Gly Val
                325

(2) INFORMATION FOR SEQ ID NO:12:

(i) SEQUENCE CHARACTERISTICS:
        (A) LENGTH: 324 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:12:

Ser Tyr Ile Cys Ser Gln Gln Asp Thr Leu Ser Asn Lys Ile Thr Glu
1               5                   10                  15

Cys Cys Lys Leu Thr Thr Leu Glu Arg Gly Gln Cys Ile Ile His Ala
            20                  25                  30

Glu Asn Asp Glu Lys Pro Glu Gly Leu Ser Pro Asn Leu Asn Arg Phe
        35                  40                  45

Leu Gly Asp Arg Asp Phe Asn Gln Phe Ser Ser Gly Glu Lys Asn Ile
    50                  55                  60

Phe Leu Ala Ser Phe Val His Glu Tyr Ser Arg Arg His Pro Gln Leu
65                  70                  75                  80

Ala Val Ser Val Ile Leu Arg Val Ala Lys Gly Tyr Gln Glu Leu Leu
                85                  90                  95

Glu Lys Cys Phe Gln Thr Glu Asn Pro Leu Glu Cys Gln Asp Lys Gly
            100                 105                 110

Glu Glu Glu Leu Gln Lys Tyr Ile Gln Glu Ser Gln Ala Leu Ala Lys
        115                 120                 125
```

```
Arg Ser Cys Gly Leu Phe Gln Lys Leu Gly Glu Tyr Tyr Leu Gln Asn
    130                 135                 140
Glu Phe Leu Val Ala Tyr Thr Lys Lys Ala Pro Gln Leu Thr Ser Ser
145                 150                 155                 160
Glu Leu Met Ala Ile Thr Arg Lys Met Ala Ala Thr Ala Ala Thr Cys
                165                 170                 175
Cys Gln Leu Ser Glu Asp Lys Leu Leu Ala Cys Gly Glu Gly Ala Ala
                180                 185                 190
Asp Ile Ile Ile Gly His Leu Cys Ile Arg His Glu Met Thr Pro Val
                195                 200                 205
Asn Pro Gly Val Gly Gln Cys Cys Thr Ser Ser Tyr Ala Asn Arg Arg
    210                 215                 220
Pro Cys Phe Ser Ser Leu Val Val Asp Glu Thr Tyr Val Pro Pro Ala
225                 230                 235                 240
Phe Ser Asp Asp Lys Phe Ile Phe His Lys Asp Leu Cys Gln Ala Gln
                245                 250                 255
Gly Val Ala Leu Gln Arg Met Lys Gln Glu Phe Leu Ile Asn Leu Val
                260                 265                 270
Lys Gln Lys Pro Gln Ile Thr Glu Glu Gln Leu Glu Ala Leu Ile Ala
        275                 280                 285
Asp Phe Ser Gly Leu Leu Glu Lys Cys Cys Gln Gly Gln Glu Gln Glu
    290                 295                 300
Val Cys Phe Ala Glu Glu Gly Gln Lys Leu Ile Ser Lys Thr Gly Ala
305                 310                 315                 320
Ala Leu Gly Val (2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:13:

Ser Tyr Ile Cys Ser Gln Gln Asp Thr
1               5

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

AAAAAAGGTA CCACACTGCA TAGAAATGAA                                      30

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:15:

AAAAAAGGAT CCTTAGCTTT CTCTTAATTC TTT                           33

(2) INFORMATION FOR SEQ ID NO:16:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

AAAAAAATCG ATATGAGCTT GTTAAATCAA CAT                           33

(2) INFORMATION FOR SEQ ID NO:17:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

AAAAAAGGAT CCTTAGCTCT CCTGGATGTA TTT                           33

(2) INFORMATION FOR SEQ ID NO:18:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

AAAAAAATCG ATATGCAAGC ATTGGCAAAG CGA                           33

(2) INFORMATION FOR SEQ ID NO:19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

AAAAAAGGAT CCTTAAACTC CCAAAGCAGC ACG                           33

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

AAAAAAATCG ATATGTCCTA CATATGTTCT CAA                           33

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GATCTAGAAT TCGGATCCGG T                              21

(2) INFORMATION FOR SEQ ID NO:22:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:22:

Asp Leu Glu Phe Met Thr Leu His Arg Asn
1              5              10

(2) INFORMATION FOR SEQ ID NO:23:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

AAAAAACTCG AGATACACTG CATAGAAATG AA                32

(2) INFORMATION FOR SEQ ID NO:24:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

AAAAAAGAAT TCTTAAACTC CCAAAGCAGC ACG              33

EXPRESSION AND PURIFICATION OF CLONED HUMAN ALPHA-FETOPROTEIN

CROSS-REFERENCE TO RELATED APPLICATIONS

This application is a continuation-in-part of Murgita, U.S. Ser. No. 08/377,317, filed Jan. 24, 1995, now abandoned, which is a continuation-in-part of Murgita, U.S. Ser. No. 08/133,773, issued as U.S. Pat. No. 5,384,250, filed, Oct. 8, 1993, which is a continuation of Murgita, U.S. Ser. No. 07/767,435, filed Sep., 27, 1991, now abandoned.

This application is also related to U.S. applications entitled *Use of Recombinant Human Alpha-Fetoprotein For Treating and Diagnosing Cancers* (U.S. Ser. No. 08/377, 311), *Use of Recombinant Human Alpha-Fetoprotein As An Immunosuppressive Agent* (U.S. Ser. No. 08/377,309), and *Use of Recombinant Human Alpha-Fetoprotein As A Cell Proliferative Agent* (U.S. Ser. No. 08/377,316), filed on Jan. 24, 1995, the disclosures of which are all hereby incorporated by reference.

BACKGROUND OF THE INVENTION

The field of the invention is expression and purification of cloned human alpha-fetoprotein.

Alpha-fetoprotein (AFP) is a serum protein normally found at significant levels only in fetal blood. In adult blood increased alpha-fetoprotein levels are associated with liver regeneration and certain carcinomas.

The specific function of alpha-fetoprotein is not known. Suggested roles for the protein include: fetal albumin; protection from maternal immune attack; and protection from maternal estrogen.

Morinaga et al. (*Proc. Natl. Acad. Sci.* USA 80:4604, 1983) report the cloning of human AFP.

Innis et al. (*Arch. Biochem. Biophys.* 195:128, 1979) report the cloning of an approximately 950 base-pair fragment of human AFP into *E. coli* plasmid pBR322.

Nishi et al. (*J. Biochem.* 104:968, 1988) report the expression of rat AFP in *E. coli* and *Saccharomyces cerevisiae*. Nishi et al. also report that, in an estradiol-binding assay, yeast-produced rat rAFP is as active a authentic AFP, while bacterial-produced rat rAFP is essentially inactive. Further, when characterized by radioimmunoassay or an Ouchterlony double immunodiffusion assay, yeast-produced rat rAFP bears a closer resemblance to authentic rat AFP than does bacterial-produced rat rAFP. Nishi et al. state that:

"In the Ouchterlony double immunodiffusion test, authentic and yeast rAFP formed a completely fused precipitin line with antibody to rat AFP while *E. coli* rAFP showed a reaction of partial identity in a similar test . . . . It is likely that the functionally active yeast rAFP in this study had the correct pairs of disulfide bridges. On the other hand the *E. coli* rAFP probably failed to form them".

Yamamoto et al. (*Life Sciences* 46:1679, 1990) report the expression of human AFP in yeast and report that the rAFP so produced was "indistinguishable immunologically from authentic AFP."

Giuliani et al. (*Protein Engineering* 2:605, 1989) report the expression of a portion of human AFP (amino acids 38 to 119) in *E. coli*.

Japanese Patent Application 88158596 reports a method for preparing recombinant human domain I AFP in *E. coli*.

SUMMARY OF THE INVENTION

In general, the invention features substantially pure biologically-active recombinant human alpha-fetoprotein produced using a prokaryotic cell. In preferred embodiments, the pure recombinant human alpha-fetoprotein of includes a sequence substantially identical to amino acids 1 to 590 of FIG. 1 (SEQ ID NO: 4).

In related aspects, the invention also features substantially pure biologically-active recombinant human alpha-fetoprotein including a sequence that is substantially identical to either amino acids 1 to 389 of FIG. 1 (SEQ ID NO: 4) or a fragment thereof; amino acids 198 to 590 of FIG. 1 (SEQ ID NO: 5) or a fragment thereof; amino acids 198 to 389 of FIG. 1 (SEQ ID NO: 6) or a fragment thereof; amino acids 390 to 590 of FIG. 1 (SEQ ID NO: 7) or a fragment thereof; and amino acids 267 to 590 of FIG. 1 (SEQ ID NO: 8) or a fragment thereof.

Such recombinant human alpha-fetoprotein may be used in therapeutic compositions.

In another related aspect, the invention features a method for using an insect cell for producing biologically active recombinant human alpha-fetoprotein or a fragment or analog thereof involving a) providing a transformed insect cell (e.g., *Spodoptera frugiperda*) including a recombinant DNA molecule encoding the human alpha-fetoprotein or fragment or analog thereof operably linked to an expression control element which directs the expression of the human alpha-fetoprotein or fragment or analog thereof;

b) culturing the transformed cell; and c) recovering the biologically active human alpha-fetoprotein or fragment or analog thereof.

The invention also features substantially pure human alpha-fetoprotein or fragment or analog thereof produced using the above-described method, and therapeutic compositions including substantially pure human alpha-fetoprotein or fragment or analog thereof produced using an insect cell.

By "human alpha-fetoprotein" is meant a polypeptide having substantially the same amino acid sequence as the protein encoded by the human alpha-fetoprotein gene. Morinaga et al. (*Proc. Natl. Acad. Sci.* USA 80:4604, 1983) reports the sequence of cDNA complementary to human alpha-fetoprotein.

By "expression control element" is meant a nucleotide sequence which includes recognition sequences for factors that control expression of a protein coding sequence to which it is operably linked. Accordingly, an expression control element generally includes sequences for controlling both transcription and translation, for example, promoters, ribosome binding sites, repressor binding sites, and activator binding sites.

By "substantially the same amino acid sequence" is meant a polypeptide that exhibits at least 80% homology with naturally occurring amino acid sequence of human alpha-fetoprotein, typically at least about 85% homology with the natural human alpha-fetoprotein sequence, more typically at least about 90% homology, usually at least about 95% homology, and more usually at least about 97% homology with the natural human alpha-fetoprotein sequence. The length of comparison sequences will generally be at least 16 amino acids, usually at least 20 amino acids, more usually at least 25 amino acids, typically at least 30 amino acids, and preferably more than 35 amino acids.

Homology, for polypeptides, is typically measured using sequence analysis software (e.g., Sequence Analysis Software Package of the Genetics Computer Group, University of Wisoonsin Biotechnology Center, 1710 University Avenue, Madison, Wis. 53705). Protein analysis software matches similar sequences by assigning degrees of homology to various substitutions, deletions, substitutions, and other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

As used herein, the term "substantially pure" describes a protein or polypeptide which has been separated from components which naturally accompany it. Typically, a protein of interest is substantially pure when at least 60% to 75% of the total protein in a sample is the protein of interest. Minor variants or chemical modifications typically share the same polypeptide sequence. A substantially pure protein will typically comprise over about 85 to 90% of the protein in sample, more usually will comprise at least about 95%, and preferably will be over about 99% pure. Normally, purity is measured on a chromatography column, polyacrylamide gel, or by HPLC analysis.

A protein is substantially free of naturally associated components when it is separated from the native contaminants which accompany it in its natural state. Thus, a protein which is chemically synthesized or produced in a cellular system different from the cell from which it naturally originates will be substantially free from its naturally associated components. Thus the term can be used to describe polypeptides and nucleic acids derived from eukaryotic organisms which have been synthesized in *E. coli* and other prokaryotes.

The present invention provides for substantially pure human alpha-fetoprotein. Various methods for the isolation of human AFP from biological material may be devised, based in part upon the structural and functional properties of human alpha-fetoprotein. Alternatively, anti-AFP antibodies may immobilized on a solid substrate to generate a highly specific affinity column for purification of human AFP.

Besides substantially full-length polypeptides, the present invention provides for biologically active recombinant fragments of alpha-fetoprotein. For example, fragments active in ligand binding or immunosuppression.

The natural or synthetic DNA fragments coding for human alpha-fetoprotein or a desired fragment thereof will be incorporated into DNA constructs capable of introduction to and expression in cell culture. DNA constructs prepared for introduction into such hosts will typically include an origin of replication which can be utilized by the host cell, a DNA fragment encoding the desired portion of human alpha-fetoprotein, transcription and translational initiation regulatory sequences operably linked to the alpha-fetoprotein encoding segment, and transcriptional and translational termination regulatory sequences operably linked to the alpha-fetoprotein encoding segment. The transcriptional regulatory sequences will typically include a heterologous promoter which is recognized by the host. The selection of an appropriate promoter will depend upon the host, but promoters such as the trp, tac and phage promoters, tRNA promoters and glycolytic enzyme promoters may be used under appropriate circumstances (Sambrook et al. eds., *Molecular Cloning: Laboratory Manual,* Cold Spring Harbor Press, Cold Spring Harbor, N.Y. 1989). In some instances it may be desirable to include appropriately positioned recognition sequences for factors capable of regulating transcription in the host cell (e.g., the lac repressor of *E. coli*). Commercially available expression vectors, which include the replication system and transcriptional and translational regulatory sequences together with convenient sites for the insertion of a DNA fragment encoding the gene to be expressed may be used.

The various promoters, transcriptional, and translational described above are generally referred to as an "expression control element".

It is also possible to integrate a DNA fragment encoding all or part of human AFP into the host cell's chromosome.

The vectors containing the DNA segments of interest can be transferred into the host cell by well-known methods, which vary depending on the type of cellular host (Sambrook et al., supra). The term "transformed cell" is meant to also include the progeny of a transformed cell.

Prokaryotic hosts useful for high level expression of recombinant proteins include: various strains of *E. coli, Bacillus subtilis,* and Pseudomonas.

The method of the invention provides a means by which to generate large quantities of human alpha-fetoprotein having biological activity. AFP produced according to the method of the invention has biological activity despite the fact that it is not modified in the same fashion as naturally occurring human AFP.

Other features and advantages of the invention will be apparent from the following description of the preferred embodiments thereof and from the claims.

The drawings will first be described.

Drawings

FIG. 1 is the nucleotide sequence (SEQ ID NO: 4) and deduced amino acid sequence (SEQ ID NO: 5) of the cDNA encoding human alpha-fetoprotein.

FIG. 2 is the SDS-PAGE analysis of rHuAFP Fragment I (SEQ ID NO: 11) (Lane A, MW marker; Lane B, natural human alpha-fetoprotein (AFP); Lane C, unpurified rHuAFP; Lane D, rHuAFP Fragment I, and Lane E, rHuAFP (amino acids 1–590 of FIG. 1, SEQ ID NO: 5).

Figure 3:
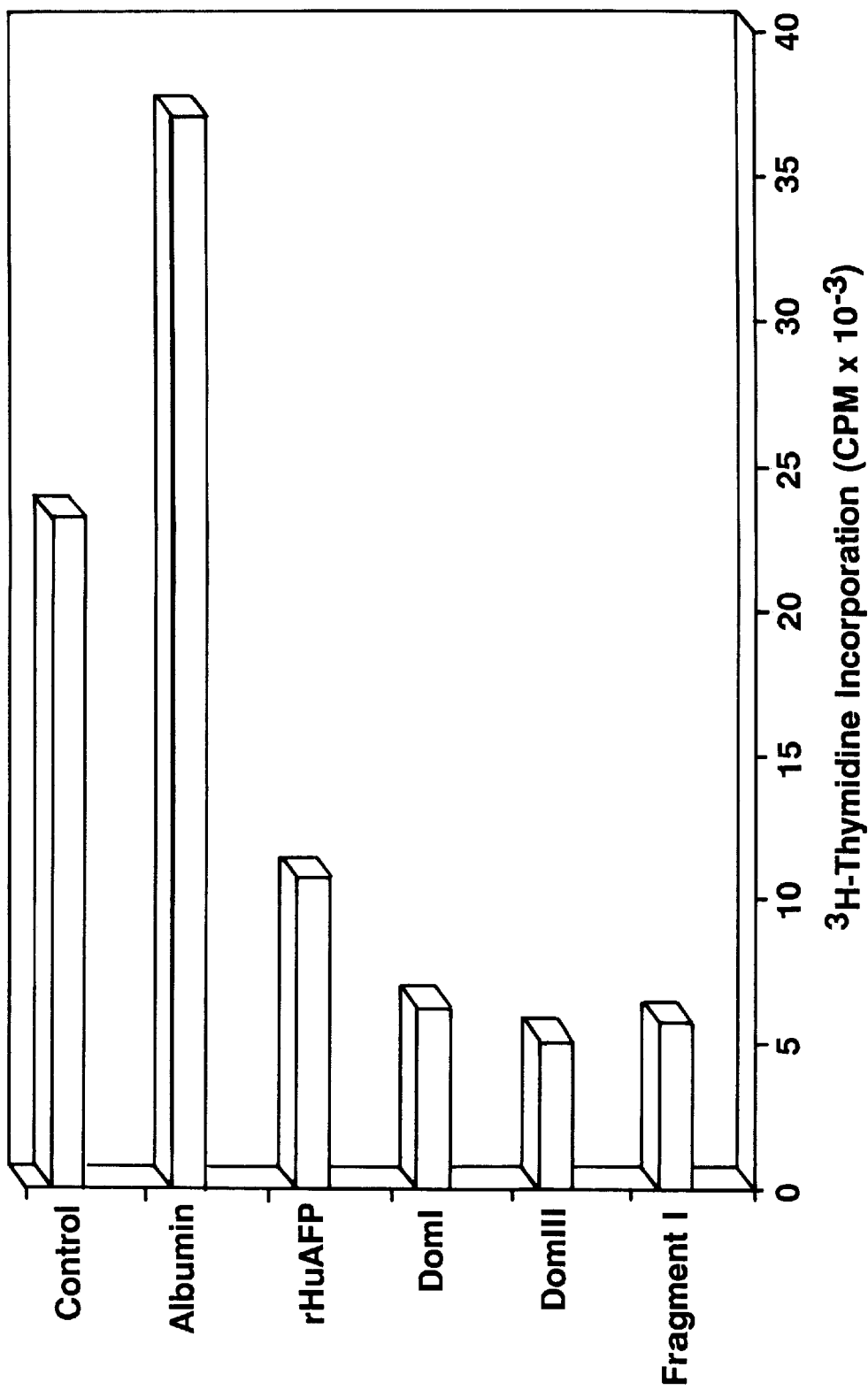

FIG. 3 is a bar graph showing the inhibition of human AMLR by *E. coli*-derived rHuAFP and domain fragments.

Figure 4A:
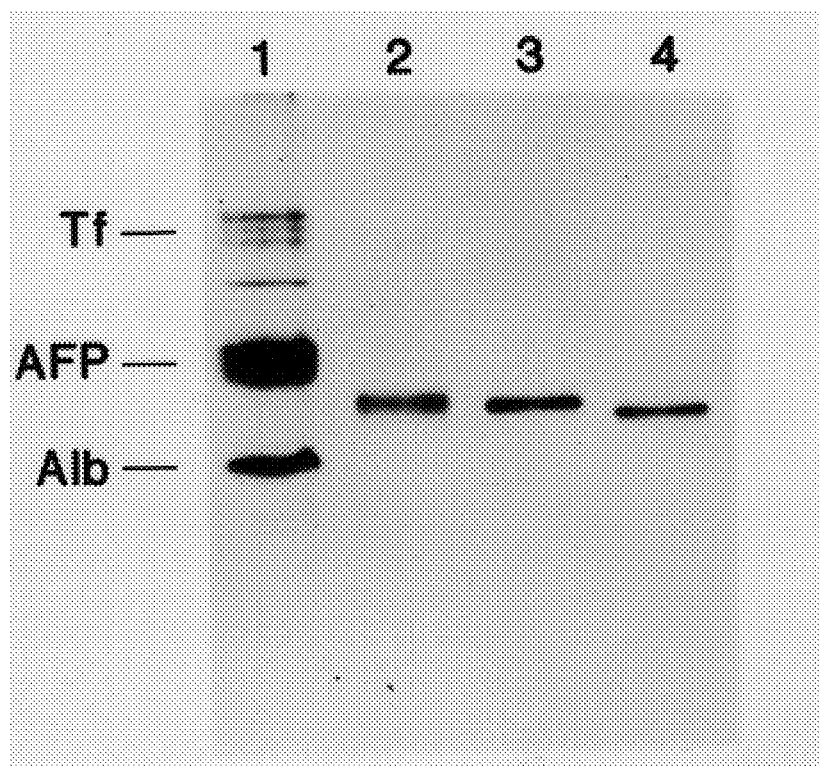
Figure 4B:
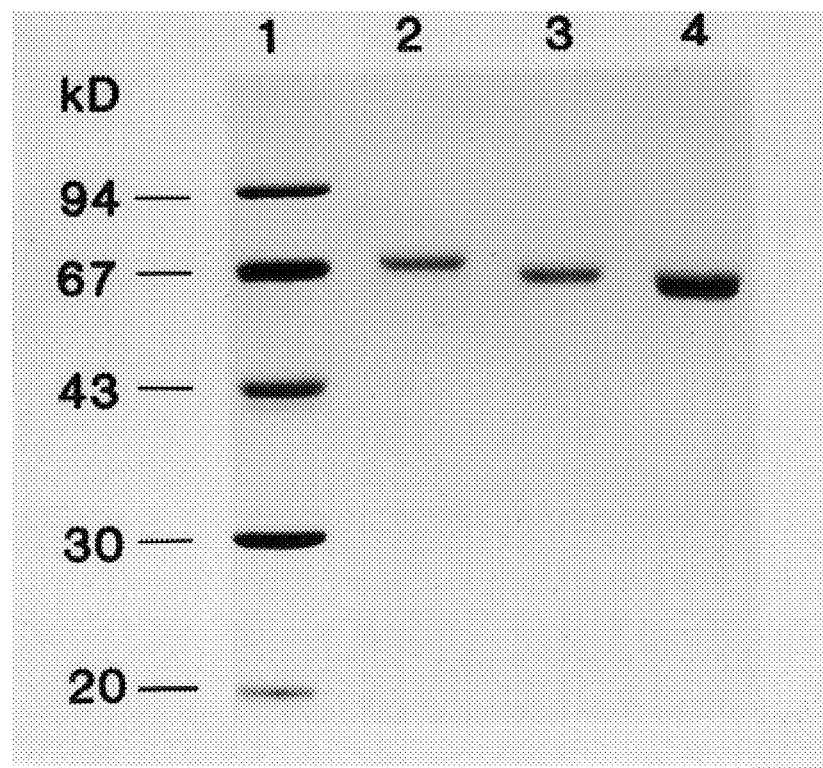

FIG. 4 is a series of graphs (FIGS. 4A–4D) showing the purity and biochemical characteristics of baculovirus- and *E. coli*-derived rHuAFP using polyacrylamide gel electrophoresis and column chromatography. FIG. 4A is a 10% non-denaturing alkaline polyacrylamide gel showing the purity of rHuAFP. Mouse amiotic fluid proteins (transferring AFP and albumin) are shown in lane 1, natural HuAFP (lane 2), baculovirus-derived rHuAFP (lane 3), and *E. coli*-derived rHuAFP (lane 4). FIG. 4B is a 10sodium dodecyl sulfate-polyacrylamide gel showing the purity of rHuAFP produced using baculovirus and *E. coli* expression systems. Molecular weight markers are shown in lane 1, natural HuAFP, baculovirus- and *E. coli*-derived rHuAFP are shown in lanes 2, 3 and 4, respectively. FIG. 4C is a series of FPLC chromatograms of natural HuAFP, baculovirus-derived and *E. coli*-derived rHuAFP eluted on a MonoQ anion exchange column. The superimposed chromatograms identify natural HuAFP (Chromatogram 1), baculovirus- and *E. coli*-derived rHuAFP (Chromatograms 2 and 3, respectively). FIG. 4D is a series of HPLC chromatograms obtained by passing 50 μg of natural and rHuAFP by passing through a reverse phase Delta Pak C18 column (Waters) and eluting with a gradient of 0–100% acetonitrile in 0.1% TFA. The superimposed chromatograms identify natural HuAFP (Chromatogram 1) and baculovirus- and *E. coli*-derived rHuAFP (Chromatograms 2 and 3, respectively).

Figure 5:
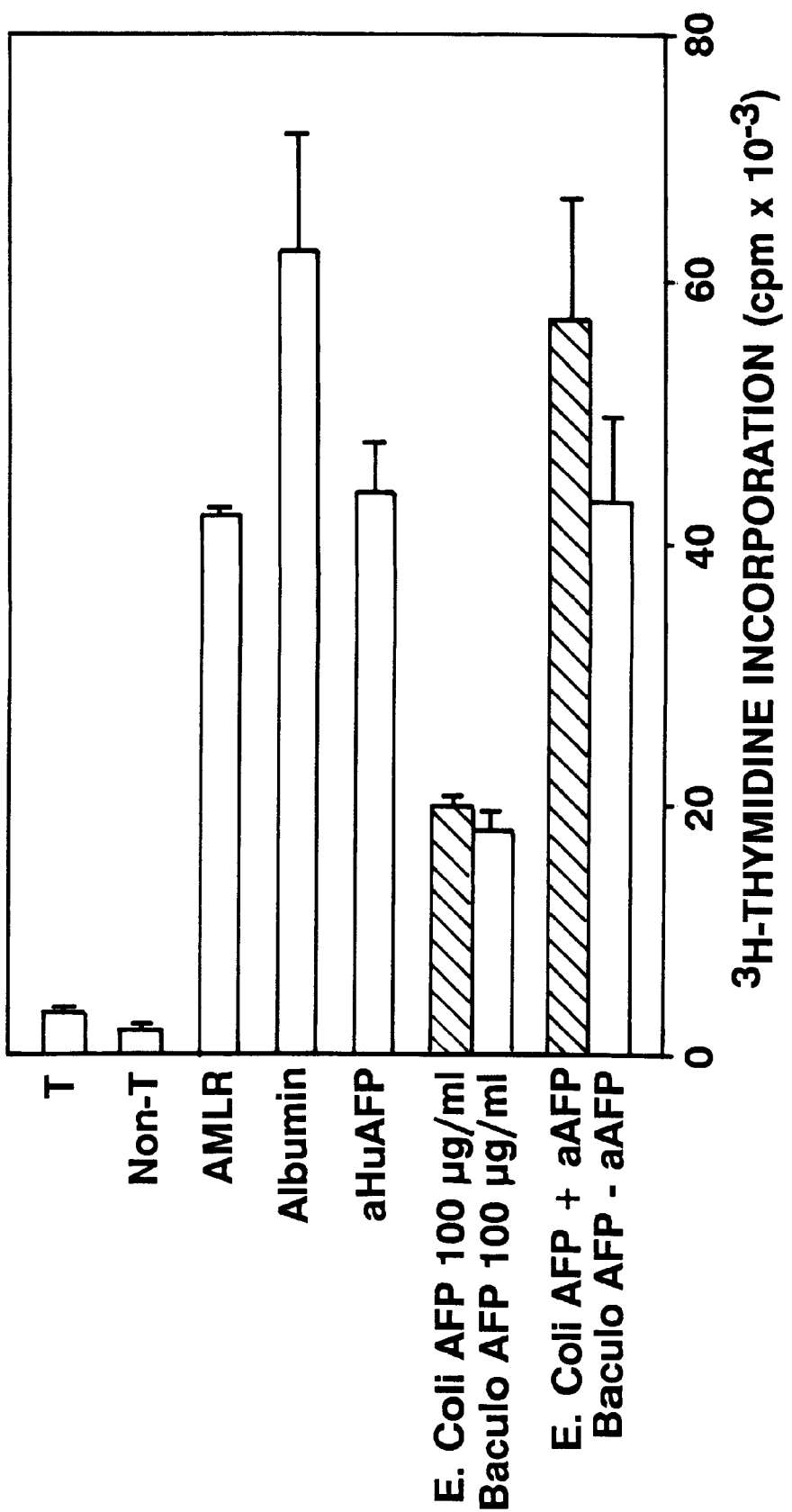

FIG. 5 is a bar graph showing that monoclonal anti-natural HuAFP antibodies block immunosuppression of the AMLR by rHuAFP produced using baculovirus and *E. coli* expression systems. Immunosuppression by rHuAFP produced using baculovirus and *E. coli* expression systems was significant (p<0.002) and blocking of rHuAFP-mediated immunosuppression by the AMLR by monoclonal anti-natural HuAFP (à AFP) antibodies was also significant (p<0.03). AMLR cultures were set up with $2\times10^5$ responding T cells with $2.5\times10^5$ irradiated autologous non-T cells in the presence or absence of protein, harvested at 144 hours, and autoproliferation was measured by the amount of $^3$H-thymidine incorporated by autoreactive T cells. Blocking of the autoproliferative effects of rHuAFP was carried out by adding murine anti-human AFP monoclonal antibodies at a dilution of ⅛ (125 μg/ml) to AMLR cultures suppressed by 100 μg/ml baculovirus derived (diagonal bars) and by 100 μg/ml of E. coli-derived (open bars) rHuAFP. Control cultures consisted of the AMLR in the presence of ⅛ dilution of anti-human AFP (à AFP) monoclonal antibodies.

Figure 6A:
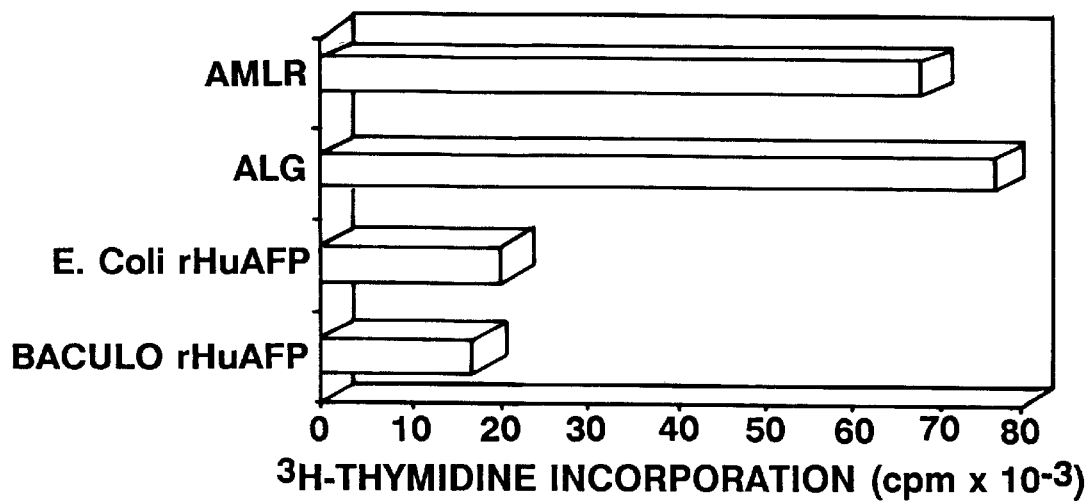
Figure 6B:
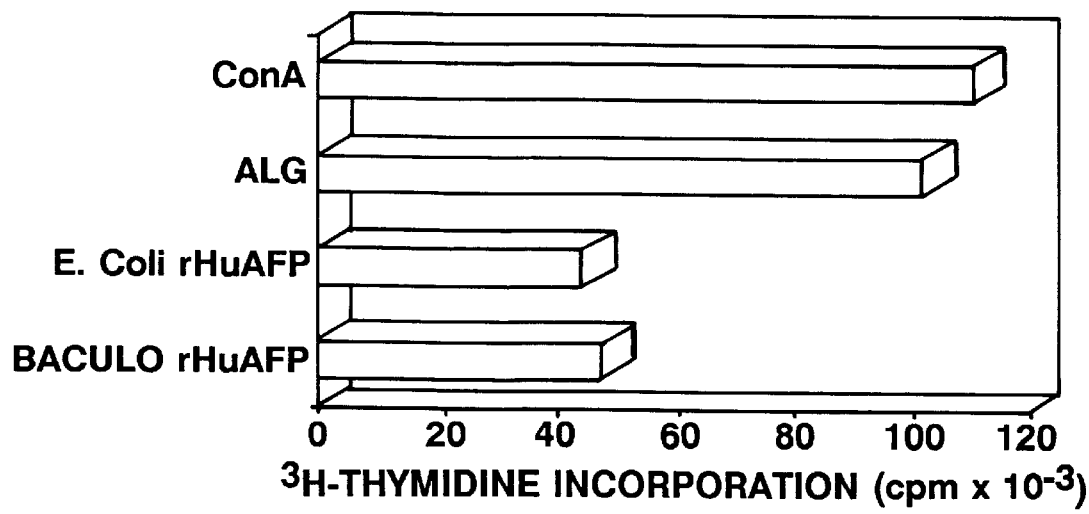

FIG. 6 is a series of bar graphs (FIGS. 6A and 6B) showing the effects of rHuAFP-mediated immunosuppression using human AMLR (FIG. 6A) and PBL (FIG. 6B) assays. FIG. 6A shows the results of autologous mixed lymphocyte reaction (AMLR) prepared by co-culturing 250,000 T cells with an equivalent amount of autologous irradiated non-T lymphocytes. Recombinant HuAFP preparations derived from E. coli and baculovirus expression systems and albumin were added at a concentration of 100 μg/ml at the initiation of culture. Proliferative responses were measured at 144 hours by $^3$H-thymidine incorporation. FIG. 6B shows the results of PBLs ($2\times10^5$) stimulated with 1 μg/ml ConA which were cultured in RPMI medium supplemented with only 2 mg/ml albumin for 48 hrs. Albumin and rHuAFP derived from E. coli and baculovirus were added to the initiation of the cultures at a concentration of 100 μg/ml. Proliferative responses were measured as the amount of $^3$H-thymidine incorporated during DNA synthesis. The SEM were determined to represent less than 5% of the value of the mean.

Figure 7:
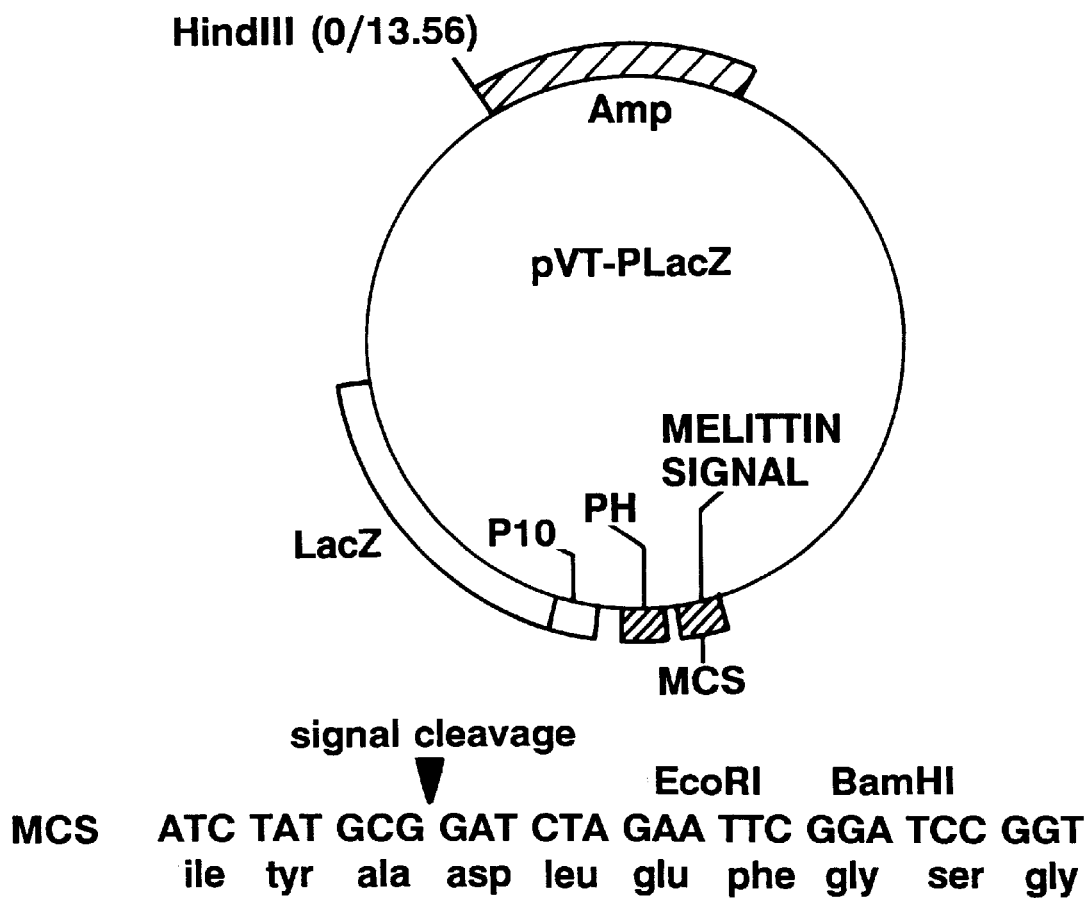

FIG. 7 is a plasmid map of pVT-PlacZ.

DETAILED DESCRIPTION

Construction of a cDNA Library

A cDNA library was constructed with size-fractionated cDNA (0.5–3 kb) prepared from poly(A)$^+$ RNA isolated from liver cells (~3 grams wet weight) of a 4.5 months old human abortus. (Alternatively, a fetal cDNA library may be obtained from Clontech Laboratories, Inc., Palo Alto, Calif.) Total RNA was prepared by the guanidium thiocyanate method (Chirgwin et al., *Biochemistry* 18:5294, 1979), and mRNA was selected by oligo(dT)-cellulose chromatography (Collaborative Research, Bedford, Mass.) (*Current Protocols in Molecular Biology*, Ausubel et al., eds., Wiley Interscience, New York, 1989). cDNA was synthesized using the Librarian II cDNA synthesis kit (Invitrogen, San Diego, Calif.) and fractionated on a 1% agarose gel. Fragments of 0.5 to 3 kb were extracted and ligated to vector pTZ18-RB (Invitrogen), and used to transform competent *E. coli* DH1αF' (Invitrogen). Colony lifts were performed with Colony/Plaque Screen filters (DuPont, Wilmington, Del.), and the transferred bacterial colonies were lysed and denatured by incubation in a solution of 0.5M NaOH, 1.5M NaCl for 10 min. The filters were washed for 5 min in 1.5M NaCl, 0.50M Tris-HCl (pH 7.6), and air dried. Filters were then washed 5 times in chloroform, soaked in 0.3M NaCl to remove cellular debris, and then air dried. The DNA was fixed to the nitrocellulose by baking at 80° under vacuum for 2 hrs. The baked filters were prehybridized for 3 hr at 37° C. in 6×SSC (1×SSC=150 mM NaCl, 15 mM sodium citrate [pH 7.0]), 1×Denhardt's solution (0.2 g/l polyvinylpyrrolidone, 0.2 g/l BSA, 0.2 g/l Ficoll 400), 0.05% sodium pyrophosphate, 0.5% SDS, and 100 μg/ml *E. coli* DNA. Hybridization was performed for 18–24 hr at 37° C. in the same solution without SDS, containing $1-2\times10^6$ cpm/ml of two oligonucleotides $^{32}$P-labelled by 5'-end phosphorylation (*Current Protocols in Molecular Biology*, supra). The sequence of the oligonucleotides used for probing the library: 5'-TGTCTGCAGGATGGGGAAAAA-3' (SEQ ID NO: 1) and 5'-CATGAAATGACTCCAGTA-3' (SEQ ID NO: 2), correspond to positions 772 to 792 and positions 1405 to 1422 of the human AFP coding sequence respectively. Filters were washed twice for 30 min at 37° C. with 6×SSC, 0.05% sodium pyrophosphate and once for 30 min at 48° C. in the same solution. Dried filters were exposed to Kodak XAR films in the presence of Du Pont Cronex Lightning Plus intensifier screens for 24–48 hr to identify positive clones. Positive clones were isolated, amplified, and subjected to Southern blot analysis (*Current Protocols in Molecular Biology*, supra). Briefly, purified DNA was hydrolyzed with the appropriate restriction enzymes, and the resulting fragments were resolved on a 1% agarose gel. The DNA was then transferred to a nitrocellulose membrane. Hybridization conditions were as described above except that a third $^{32}$p-labelled oligonucleotide (5'-CATAGAAATGAATATGGA-3' (SEQ ID NO: 3), representing positions 7 to 24 of the human AFP coding region) was used in addition to the other two probes described above. Five positive clones were identified among the 3,000 colonies screened. One clone, pLHuAFP, was used in the construction described below.

Construction of Full Length Human AFP cDNA

A construct containing a translation initiation codon followed by the human AFP coding sequence and a translation termination codon was created using the following five DNA fragments.

Fragment 1: Two unphosphorylated oligonucleotides were annealed to form a double-stranded DNA molecule consisting of a 5'-end cohesive EcoRI recognition site, followed by an ATG initiation codon and the first 60 bp of the human AFP cDNA up to and including the PstI restriction site located at position 60 in the coding sequence (In this scheme, nucleotide 1 is the first nucleotide of the first codon (Thr) in the mature protein and corresponds to nucleotide 102 of Morinaga et al., supra). This fragment was ligated to pUC119 (pUC19 with the intergenic region of M13 from HgiA I at 5465 to AhaII at 5941 inserted at the Nde I site of pUC19) linearized with Eco RI and Pst I. The resulting DNA was amplified in *E. coli* NM522 (Pharmacia, Piscataway, N.J.) The EcoRI-PstI insert was recovered by enzymatic digestion of the recombinant plasmid followed by electrophoretic separation on a 5% polyacrylamide gel and isolation from the gel.

Fragment 2: A 97 bp human AFP cDNA fragment (positions 57 to 153) was obtained by digesting pLHuAFP with PstI and NsiI and gel purifying as described above. This clone contains the entire coding region of human AFP as well as 5' and 3' untranslated sequences.

Fragment 3: A 224 bp human AFP cDNA fragment (positions 150 to 373) was obtained by digesting pLHuAFP with NsiI and AlwNI and purifying as described above.

Fragment 4: A 1322 bp human AFP cDNA fragment (positions 371 to 1692) was obtained by digesting pLHuAFP with AlwNI and StyI and purifying as described above.

Fragment 5: Two unphosphorylated oligonucleotides were annealed to form a 86 bp double-stranded DNA contains the human AFP sequence from position 1693 in the StyI site to the TAA termination codon that ends the AFP coding region at position 1773, followed by a cohesive BamHI site. This synthetic DNA was used without any further manipulations.

pBlueScript (StrataGene, La Jolla, Calif.) was completely hydrolyzed with EcoRI and BamHI, and added to ligation mixture containing the five purified fragments described above. A control ligation contained only the linearized pBluescript. Portions of these two ligation mixtures were used to transform competent *E. coli* DH5α (GIBCO/BRL, Grand Island, N.Y.). Recombinant plasmids were isolated from several transformants and screened by extensive restriction enzyme analysis and DNA sequencing. One recombinant plasmid was selected and termed pHuAFP. It was used for subsequent insertion of the human AFP gene into several expression vectors. pHuAFP includes a unique EcoRI-BamHI fragment that contains the complete coding sequence for human AFP in addition to an ATG start codon at the 5'-end and a TAA stop codon at the 3'-end.

AFP Expression Vectors

Successful high-level synthesis of human AFP in *E. coli* was achieved in three different expression systems. The TRP system gave direct expression. The RX1 system yielded a fusion protein containing 20 amino acids encoded by trpE and vector sequences. The MAL system expressed AFP fused to the malE gene product, a 42 kd maltose-binding protein.

TRP Expression System: The 1186 bp EcoRI-BamHI AFP encoding fragment of pHuAFP was cloned into the expression vector pTrp4 (Olsen et al., *J. Biotechnol.* 9:179, 1989) downstream of the trp promoter and a modified ribosome-binding site.

Briefly, pHuAFP was digested with EcoRI and BamHI, and the ends were filled using Klenow polymerase. The 1186 bp AFP fragment was then gel purified. pTrp4 was ClaI digested, the ends were filled using Klenow polymerase, and the linearized vector was gel purified. The 1186 bp AFP fragment and pTrp4 backbone were ligated and used to transform competent *E. coli* of the following strains: DH5α, BL21 (F. W. Studier, Brookhaven National Laboratory, Upton, N.Y.), SG927 (American Type Culture Collection, Rockville, Md.: Acc. No. 39627), SG928 (ATCC Acc. No. 39628), and SG935 (ATCC Acc. No. 39623).

RX1 Expression System: Human AFP cDNA was cloned into the expression vector PRX1 (Rimm et al., *Gene* 75:323, 1989) adjacent to the trp promoter and in the translation frame of TrpE. The human AFP cDNA was excised from pHuAFP by digestion with EcoRI and BamHI and cloned into suitably treated pRX1 (BioRad Laboratories, Hercules, Calif.). The *E. coli* strains described above and CAG456 (D. W. Cleveland, Johns Hopkins University, Baltimore, Md.) were then transformed with the final plasmid construction identified as pRX1/HuAFP.

MAL Expression System: AFP cDNA was into inserted in the expression vector pMAL (New England Biolabs, Inc., Beverly, Mass.) under control of the tac promoter and in the translation frame of MalE. Briefly, pHuAFP was hydrolysed with BamHI and the ends made blunt using Klenow polymerase. The human AFP cDNA was released from the rest of the plasmid DNA by EcoRI digestion and then gel purified. The purified fragment was ligated to appropriately digested pMAL-C. A correctly oriented recombinant plasmid, designated pMAL/HuAFP, was used to transform *E. coli* DH5α, TBI (New England Biolabs) and SG935.

The AFP coding region used in the construction of the three expression vectors was sequenced and found to encode full length AFP.

Expression of AFP in *E. coli*

Bacterial cultures were incubated at 30° C. or 37° C. with aeration. Overnight cultures of *E. coli* were grown in LB medium supplemented with the appropriate antibiotics as required (Tetracycline-HCl was at 50 $\mu$g/ml, and ampicillin-Na was at 100 $\mu$g/ml).

TRP and RX1 Expression Systems: The trp promoter was induced under tryptophan starvation conditions. Induction was performed in M9CA medium prepared as follows: 1 g Casamino acids (Difco Laboratories, Detroit, Mich.), 6 g $Na_2HPO_4$, 3 g $KH_2PO_4$, 0.5 g NaCl, 1 g $NH_4Cl$ is added to one liter milli-Q water (Millipore Corp., Bedford, Mass.), the pH adjusted to 7.4 and the solution autoclaved. The cooled medium is made 2 mM $MgSO_4$, 0.1mM $CaCl_2$, and 0.2% glucose. After a 100-fold dilution of an overnight culture in M9CA supplemented with antibiotics, the cells were grown at 30° C. to $A_{550}$ of 0.4, harvested by centrifugation, and stored as pellets at −20° C.

MAL Expression System: The tac promoter was induced with the gratuitous inducer IPTG. Overnight cultures were diluted 100-fold in LB medium supplemented with antibiotics, and the cells grown at 37° C. to $A_{550}$ of 0.4. IPTG was then added to a final concentration of 0.3 mM, and the bacteria incubated an additional 2 hr. The cells were then harvested by centrifugation and stored as pellets at −20° C.

Detection of AFP Expressed in *E. coli*

Analytical studies were performed to determine the expression and behavior of recombinant AFP. Cell pellets were either suspended in SDS-lysis solution (0.16M Tris-HCl [pH 6.8], 4% w/v SDS, 0.2M DTT, 20% glycerol, 0.02% bromophenol blue), boiled for 5 min, and used for analysis by SDS-PAGE or suspended in a lysis buffer consisting of 10 mM $Na_2HPO_4$, 30 mM NaCl, 0.25% Tween 20, 10 mM EDTA, 10 mM EGTA and incubated with 1 mg/ml lysozyme at 4° C. for 30 min prior to sonication in pulse mode for 3×1 min at 50% power (Sonics and Materials, Danbury, Conn.: model VC300 sonifier). The lysate was centrifuged at 10,000 g for 20 min, and the supernatant containing soluble protein was decanted in a separate test tube and frozen at −20° C. until used. The pellet containing insoluble protein was resuspended in SDS-lysis buffer, boiled for 5 min and kept at −20° C. until used. Total protein released in SDS-lysis buffer, as well as soluble and pellet fractions were analyzed by SDS-PAGE and immunological detection following western blot transfer. In these studies Coomassie blue stained gels were routinely scanned with a video densitometer (BioRad, model 620). This allowed a qualitative assessment of the amount of recombinant AFP produced as a percentage of total cellular protein.

Purification of AFP Expressed in the TRP System

All procedures were carried out at 4° C., unless otherwise stated. Each frozen cell pellet from a one liter culture was resuspended in 25 ml of lysis buffer A, 50 mM Tris-HCl [pH 7.5], 20% sucrose, 100 $\mu$g/ml lysozyme, 10 $\mu$g/ml PMSF), and incubated for 10 min. EDTA was added to a final concentration of 35 mM, and the extract allowed to stand a further 10 min. Following the addition of 25 ml of lysis buffer B (50 mM Tris-HCl [pH 7.5], 25 mM EDTA, 0.2% Triton X-100), the lysate was incubated an additional 30 min. The cell lysate was centrifuged at 12,000 g for 20 min, and the precipitate containing the recombinant AFP was washed twice with 50 ml of wash buffer (50 mM Tris-HCl [pH 8.0], 10 mM EDTA, 0.2% Triton X-100), followed each time by centrifugation as above. The precipitate was dissolved in 50 ml of denaturation buffer (0.1M $K_2HPO_4$ [pH 8.5], 6M guanidine-HCl, 0.1M 2-mercaptoethanol), sonicated, and then mixed on a Nutator (Clay Adams) for 4 hr. The solubilized extract was diluted 50-fold in 50 mM Tris-HCl, 100 mM NaCl, 1 mM EDTA, and the recombinant AFP protein allowed to renature for 24 hr. This 50-fold dilution step is important because prior to dilution AFP appears to be microaggregated. Subsequent to dilution and reconcentration, AFP is not aggregated. The solution was concentrated 100-fold on YM10 membranes using an Amicon filtration unit, and clarified through a Millex 0.22 $\mu$m membrane filter (Millipore). The recombinant AFP was further purified at room temperature on a Mono Q column (Pharmacia) equilibrated in 20 mM Tris-HCl (pH 8.0) with bound proteins eluted using a linear gradient of 0–100% 1M NaCl, 2 mM Tris-HCl (pH 8.0). Fractions were analyzed by SDS-PAGE, APAGE, and Western blotting.

These general techniques of polypeptide expression and purification can also be used to produce and isolate useful human alpha-fetoprotein fragments or analogs (described below).

Polyacrylamide Gel Electrophoresis and Western Immunodetection Procedures

SDS-PAGE in discontinuous buffer system and alkaline-PAGE were performed according to Hames et al. (*Gel Electrophoresis of Proteins: A Practical Approach*, IRL Press, London, 1981) using the mini-Protean electrophoresis apparatus (BioRad). Immunological detection of recombinant human AFP following SDS-PAGE or APAGE was accomplished by soaking the gels in transfer buffer (12.5 mM Tris-HCl, 96 mM glycine, 20% methanol [pH 8.2]) for 15 min. Individual gels were then layered with an Immobilon PVDF membrane (Millipore) and sandwiched between the two electrode grids of the mini-Protean transfer device (BioRad), with the gels adjacent to the cathode. The system was immersed in transfer buffer, and a 150 mA current was applied for 2 hr. Unreacted sites on the Immobilon PVDF sheets were blocked in 20 mM Tris-HCl (pH 7.5), 500 mM NaCl, 3% gelatin for 1 hr. Rabbit anti-human AFP antiserum and goat anti-rabbit IgG antibodies conjugated to alkaline phosphatase (BioRad) were used as the primary and the secondary antibodies, respectively. The alkaline phosphatase activity was detected using 5-brome-4-chloro-3-indolyl phosphate and p-nitroblue tetrazolium (Bio-Rad).

Quantitation of AFP Expression

Recombinant human AFP was quantitated using a human AFP ELISA kit (Abbott Laboratories, Chicago, Ill.).

AFP yield was estimated by scanning silver stained gels. When SG935 cells are transformed with the AFP encoding plasmid that employs the Trp expression system, AFP represents 2 to 5% of total cellular *E. coli* protein (approximately 3–7 mg AFP per liter of culture). As described above, most AFP in the initial extract is insoluble. The above-described resolubilization procedure permits 50–60% recovery of AFP in the form of stable, semi-purified, monomeric AFP (approximate yield 50 mg/20 l of *E. coli*). This can be further purified to yield 25 mg of pure monomeric AFP.

N-Terminal Analysis

Automatic Edman degradations were performed using a Porton protein/peptide gas phase microsequencer with an integrated customized microbore HPLC to optimize sequence. Protein sequence analysis was aided by the use of selected programs within the PC/Gene software package (Intelligenetics).

Fragments and Analogs

The invention includes biologically active fragments of rHuAFP. A biologically active fragment of rHuAFP, like the full-length molecule itself, is one that possesses at least one of the following activities: (a) directs a specific interaction with a target cell, e.g., binds to a cell expressing a receptor which is recognized by rHuAFP (e.g., the membrane of a cancer cell such as an MCF-7 or a bone marrow cell); (b) halts, reduces, or inhibits the growth of a neoplasm or an autoreactive immune cell (e.g., binds to a cell surface receptor and imparts an anti-proliferative signal); stimulates, increases, expands, or otherwise causes the proliferation of a cell such as a bone marrow cell (e.g., binds to a cell surface receptor a proliferative or stimulating-signal); or blocks or inhibits or prevents an immunopathologic antibody reaction. The ability of rHuAFP fragments or analogs to bind to a receptor which is recognized rHuAFP can be tested using any standard binding assay known in the art. Biological activity of such fragments and analogs are tested according to methods known in the art.

In general, fragments of rHuAFP are produced according to the techniques of polypeptide expression and purification described infra. For example, suitable fragments of rHuAFP can be produced by transformation of a suitable host cell with part of an HuAFP-encoding cDNA fragment (e.g., the cDNA described above) in a suitable expression vehicle. Alternatively, such fragments can be generated by standard techniques of PCR and cloned into the expression vectors (supra). Accordingly, once a fragment of rHuAFP is expressed, it may be isolated by various chromatographic and/or immunological methods known in the art. Lysis and fractionation of rHuAFP-containing cells prior to affinity chromatography may be performed by standard methods. Once isolated, the recombinant protein can, if desired, be further purified, e.g., by high performance liquid chromatography (see, e.g., Fisher, *Laboratory Techniques In Biochemistry And Molecular Biology*, Work and Burdon, eds., Elsevier, 1980).

As is discussed above, a rHuAFP fragment may also be expressed as a fusion protein with maltose binding protein produced in a host cell, e.g., *E. coli* or *Spodoptera frugiperda*. Using the maltose binding protein fusion and purification system (New England Biolabs, Beverly, Mass.), the cloned human cDNA sequence can be inserted downstream and in frame of the gene encoding maltose binding protein (malE), and the malE fusion protein can then be overexpressed. In the absence of convenient restriction sites in the human cDNA sequence, PCR can be used to introduce restriction sites compatible with the vector at the 5' and 3' end of the cDNA fragment to facilitate insertion of the cDNA fragment into the vector.

Following expression of the fusion protein, it can be purified by affinity chromatography. For example, the fusion protein can be purified by virtue of the ability of the maltose binding protein portion of the fusion protein to bind to amylose immobilized on a column.

To facilitate protein purification, the pMalE plasmid contains a factor Xa cleavage site upstream of the site into which the cDNA is inserted into the vector. Thus, the fusion protein purified as described above can then be cleaved with factor Xa to separate the maltose binding protein from a fragment of the recombinant human cDNA gene product. The cleavage products can be subjected to further chromatography to purify rHuAFP from the maltose binding protein. Alternatively, a fragment of rHuAFP may be expressed as a fusion protein containing a polyhistidine tag can be produced. Such a HuAFP fusion protein may then be isolated by binding of the polyhistidine tag to an affinity column having a nickel moiety which binds the polyhistidine region with high affinity. The fusion protein may then be eluted by shifting the pH within the affinity column. The rHuAFP can be released from the polyhistidine sequences present in the resultant fusion protein by cleavage of the fusion protein with specific proteases.

Recombinant HuAFP fragment expression products (e.g., produced by any of the expression systems described supra)

may be assayed by immunological procedures, such as Western blot, immunoprecipitation analysis of recombinant cell extracts, or immunofluorescence (using, e.g., the methods described in Ausubel et al., *Current Protocols In Molecular Biology*, Greene Publishing Associates and Wiley Interscience (John Wiley & Sons), New York, 1994).

Once a fragment of rHuAFP is expressed, it is isolated using the methods described supra. Once isolated, the fragment of rHuAFP can, if desired, be further purified by using the techniques described supra. Fragments, if desired, can also be produced by chemical synthesis (e.g., by the methods described in *Solid Phase Peptide Synthesis*, 2nd ed., 1984, The Pierce Chemical Co., Rockford, Ill.). The ability of a candidate rHuAFP fragment to exhibit a biological activity of alpha-fetoprotein is assessed by methods known to those skilled in the art (e.g., those described herein).

The purified recombinant gene product or fragment thereof can then be used to raise polyclonal or monoclonal antibodies against the recombinant human alpha-fetoprotein using well-known methods (see Coligan et al., eds., *Current Protocols in Immunology*, 1992, Greene Publishing Associates and Wiley-Interscience). To generate monoclonal antibodies, a mouse can be immunized with the recombinant protein, and antibody-secreting B cells isolated and immortalized with a non-secretory myeloma cell fusion partner. Hybridomas are then screened for production of recombinant human alpha-fetoprotein (or a fragment or analog thereof)-specific antibodies and cloned to obtain a homogenous cell population which produces monoclonal antibodies.

As used herein, the term "fragment," as applied to a rHuAFP polypeptide, refers to at least 20 contiguous amino acids, preferably at least 50 contiguous amino acids, more preferably at least 100 contiguous amino acids, and most preferably at least 200 to 400 or more contiguous amino acids in length of HuAFP. Fragments of rHuAFP molecules can also be generated by methods known to those skilled in the art, e.g., proteolytic cleavage or expression of recombinant peptides, or may result from normal protein processing (e.g., removal of amino acids from nascent polypeptide that are not required for biological activity).

Recombinant HuAFP fragments of interest include, but are not limited to, Domain I (amino acids 1 (Thr)—197 (Ser), see FIG. 1, SEQ ID NO: 6), Domain II (amino acids 198 (Ser)—389 (Ser), see FIG. 1, SEQ ID NO: 7), Domain III (amino acids 390 (Gln)—590 (Val), see FIG. 1, SEQ ID NO: 8), Domain I+II (amino acids 1 (Thr)—389 (Ser), see FIG. 1, SEQ ID NO: 9), Domain II+III (amino acids 198 (Ser)—590 (Val), see FIG. 1, SEQ ID NO: 10), and rHuAFP Fragment I (amino acids 266 (Met)—590 (Val), see FIG. 1, SEQ ID NO: 11). Activity of a HuAFP fragment is evaluated experimentally using conventional techniques and assays, e.g., the assays described herein.

The invention further includes analogs of full-length rHuAFP or fragments thereof. Analogs can differ from rHuAFP by amino acid sequence differences, or by modifications (e.g., post-translational modifications) which do not affect sequence, or by both. Analogs of the invention will generally exhibit at least 80%, more preferably 85%, and most preferably 90% or even 99% amino acid identity with all or part of a rHuAFP amino acid sequence. Modifications (which do not normally alter primary sequence) include in vivo, or in vitro chemical derivatization of polypeptides, e.g., acetylation, or carboxylation; such modifications may occur during polypeptide synthesis or processing or following treatment with isolated modifying enzymes. Analogs can also differ from the naturally occurring rHuAFP by alterations in primary sequence, for example, substitution of one amino acid for another with similar characteristics (e.g., valine for glycine, arginine for lysine, etc.) or by one or more non-conservative amino acid substitutions, deletions, or insertions which do not abolish the polypeptide's biological activity. These include genetic variants, both natural and induced (for example, resulting from random mutagenesis by irradiation or exposure to ethanemethylsulfate or by site-specific mutagenesis as described in Sambrook et al., *Molecular Cloning: A Laboratory Manual*, 2nd ed., Cold Spring Harbor Press, 1989, or Ausubel et al., supra). Also included are cyclized peptide molecules and analogs which contain residues other than L-amino acids, e.g., D-amino acids or non-naturally occurring or synthetic amino acids, e.g., β or γ amino acids, or L-amino acids with non-natural side chains (see e.g., Noren et al., *Science* 244:182, 1989). Methods for site-specific incorporation of non-natural amino acids into the protein backbone of proteins is described, e.g., in Ellman et al., *Science* 255:197, 1992. Also included are chemically synthesized polypeptides or peptides with modified peptide bonds (e.g., non-peptide bonds as described in U.S. Pat. Nos. 4,897,445 and 5,059,653) or modified side chains to obtain the desired pharmaceutical properties as described herein. Useful mutants and analogs are identified using conventional methods, e.g., those described herein.

The cloning, expression, isolation and characterization of exemplary rHuAFP fragments now follows. These examples are provided to illustrate, not limit, the invention.

Experimental

Materials and Methods

Polymerase Chain Reaction (PCR) rHuAFP Fragments

Plasmid constructs encoding fragments of human alpha-fetoprotein were prepared using polymerase chain reaction (PCR) techniques known to those skilled in the art of molecular biology, using oligonucleotide primers designed to amplify specific portions of the human alpha-fetoprotein gene (see e.g., *PCR Technology*, H. A. Erlich, ed., Stockton Press, New York, 1989; *PCR Protocols: A Guide to Methods and Applications*, M. A. Innis, David H. Gelfand, John J. Sninsky, and Thomas J. White, eds., Academic Press, Inc., New York, 1990, and Ausubel et. al., supra).

The following six rHuAFP fragments were prepared to evaluate their biological activity (e.g., according to the methods disclosed herein):

| | | |
|---|---|---|
| Domain I | Amino acids 1 (Thr) - 197 (Ser), | (FIG. 1, SEQ ID NO: 6) |
| Domain II | Amino acids 198 (Ser) - 389 (Ser), | (FIG. 1, SEQ ID NO: 7) |
| Domain III | Amino acids 390 (Gln) - 590 (Val), | (FIG. 1, SEQ ID NO: 8) |
| Domain I + II | Amino acids 1 (Thr) - 389 (Ser), | (FIG. 1, SEQ ID NO: 9) |
| Domain II + III | Amino acids 198 (Ser) - 590 (Val), | (FIG. 1, SEQ ID NO: 10) |
| rHuAFP Fragment I | Amino acids 266 (Met) - 590 (Val), | (FIG. 1, SEQ ID NO: 11) |

Amino acids sequences were deduced from those shown for human alpha-fetoprotein (1(Thr)—590 (Val); SEQ ID NO: 5 in FIG. 1. Fragments of rHuAFP designated Domain I, Domain II, Domain III, Domain I+II, Domain II+III and rHuAFP Fragment I were synthesized using standard PCR reaction conditions in 100 µL reactions containing 34 µL $H_2O$, 10 µL 10× reaction buffer, 20 µL 1 mM dNTP, 2 µL DNA template (HuAFP cloned in pI18), appropriate 5' and 3' oligonucleotide primers (10 μL 10 pmol/μL 5' primer, 10 μL 10 pmol/μL 3' primer), 1 μL glycerol, 10 μL DMSO, and 1 μL Pfu polymerase (Stratagene, LaJolla, Calif.). Primers used for PCR amplifications were:

| | | |
|---|---|---|
| DomI25 | 5'-AAAAAAGGTACCACACTGCATAGAAATGAA-3' | (SEQ ID NO: 14) |
| DomI3 | 5'-AAAAAAGGATCCTTAGCTTTCTCTTAATTCTTT-3' | (SEQ ID NO: 15) |
| DomII5 | 5-'AAAAAAATCGATATGAGCTTGTTAAATCAACAT-3' | (SEQ ID NO: 16) |
| DomII3 | 5'-AAAAAAGGATCCTTAGCTCTCCTGGATGTATTT-3' | (SEQ ID NO: 17) |
| DomIII5 | 5'-AAAAAATCGATATGCAAGCATTGGCAAGCGA-3' | (SEQ ID NO: 18) |
| DomIII3 | 5'-AAAAAGGATCCTTAAACTCCCAAAGCAGCACG-3' | (SEQ ID NO: 19) |
| 5'rHuAFP Fragment I | 5'-AAAAAAATCGATATGTCCTACATATGTTCTCAA-3' | (SEQ ID NO: 20) |

Accordingly, primer pairs DomI25 and DomI3, DomII5 and DomII3, DomIII5 and DomIII3, 5'rHuAFP Fragment I and DomIII3, DomI25 and DomII3, and DomII5 and DomIII3 were used to isolate cDNA sequences of Domain I, Domain II, Domain III, rHuAFP Fragment I, Domain I+II, and Domain II+III, respectively, of rHuAFP. Annealing, extension, and denaturation temperatures were 50° C., 72° C., and 94° C., respectively, for 30 cycles. PCR products were purified according to standard methods. Purified PCR products encoding Domain I and Domain I+II were digested individually with KpnI and BamHI and cloned separately into KpnI/BamHI-treated pTrp4. Purified PCR products encoding Domain II, Domain III, Domain II+III, and rHuAFP Fragment I were digested individually with Bsp106I and BamHI and were cloned separately into Bsp106I/BamHI-treated pTrp4. Each plasmid construct was subsequently transformed into competent *E. coli* cells. Since the expression product will begin with the amino acid sequence encoded by the translation start signal methionine, it is expected that such signal will be removed, or in any event, not affect the bioactivity of the ultimate expression product.

Autologous Mixed Lymphocyte Reactions (AMLR)

Isolation of human peripheral blood mononuclear cells (PBMC), their fractionation into non-T cell populations, and the AMLR, were performed according to standard procedures. Responder T cells were isolated by passing $1.5 \times 10^8$ PMBC over a commercial Ig-anti-Ig affinity column (Biotek Laboratories) and $2 \times 10^5$ responder cells were subsequently cultured with $2 \times 10^5$ autologous $^{137}$Cs-irradiated (2500 rads) non-T stimulator cells from a single donor. The medium employed consisted of RPMI-1640 supplemented with 20 mM HEPES (Gibco), $5 \times 10^{-5}$ M 2-mercaptoethanol (BDH, Montreal, QC), 4 mM L-glutamine (Gibco), 100 U/ml penicillin (Gibco) and 100 μg/ml streptomycin sulfate, with the addition of 10% fresh human serum autologous to the responder T cell donor for the AMLR. Varying concentrations of purified rHuAFP, human serum albumin (HSA), anti-HuAFP monoclonal antibodies clone #164 (125 μg/ml final concentration in culture) (Leinco Technologies, St. Louis, Mo.) were added at the initiation of cultures. AMLR cultures were incubated for 4 to 7 days, at 37° C. in 95% air and 5% $CO_2$. At the indicated intervals, DNA synthesis was assayed by a 6 hour pulse with 1 μCi of $^3$H-thymidine (specific activity 56 to 80 Ci/mmole, ICN). The cultures were harvested on a multiple sample harvester (Skatron, Sterling, Va.), and the incorporation of $^3$H-TdR was measured in a Packard 2500 TR liquid scintillation counter. Results are expressed as mean cpm±the standard error of the mean of triplicate or quadruplicate cultures.

Peripheral Blood Lymphocyte (PBL) Assays

Heparinized blood from normal donors was diluted 1:1 with PBS and human peripheral blood lymphocytes (PBL) were separated from red blood cells by density centrifugation on Ficoll-Hypaque (Sigma, St. Louis, Mo.). They were washed at least 3 times with PBS and verified for cell viability by the Trypan Blue exclusion method. Human PBL ($2.5 \times 10^5$ cells) were cultured according to standard methods. Results are expressed as the mean cpm thymidine incorporation±SEM of triplicate cultures.

Results

Expression and Purification

*E. coli* containing the expression plasmid encoding rHuAFP were cultured as described above. FIG. 2 (lane D) shows the SDS-PAGE profile of purified rHuAFP Fragment I. N-terminal amino acid sequence analysis showed that rHuAFP Fragment I possessed the amino acid sequence $Ser_{267}$-Tyr-Ile-Cys-Ser-Gln-Gln-Asp-$Thr_{275}$ (SEQ ID NO: 13) which corresponds to the expected N-terminal amino acid sequence of rHuAFP Fragment I (see FIG. 1, SEQ ID NO: 11) where the initiating methionine is cleaved intracellularly.

Inhibition of the Autologous Mixed Lymphocyte Reactions (AMLR)

The immunosuppressive activity of 100 μg/ml rHuAFP Fragment I was assessed by its ability to suppress human autologous mixed lymphocyte reactions (AMLR). As shown in Table I and FIG. 3, rHuAFP Fragment I inhibited the proliferative response of autoreactive lymphocytes stimulated by autologous non-T cells at 144 hours. In addition, as shown in FIG. 3, Domains I and III also inhibited the AMLR.

TABLE I

| Reaction Setup | Thymidine Incorporation (CPM) |
|---|---|
| T Cells | 7118 ± 964 |
| AMLR | 83103 ± 6480 |
| AMLR + rHuAFP Fragment I (100 μg/ml) | 29692 ± 2963 |

Inhibition of the Peripheral Blood Lymphocytes Reactions (PBL)

The immunosuppressive activity of 100 μg/ml rHuAFP Fragment I, and *E. coli*- and baculovirus-derived rHuAFP (described below) was also assessed for the ability to suppress human peripheral blood lymphocyte reactions (PBL). As shown in Table II, *E. coli*- and baculovirus-derived rHuAFP and Fragment I (produced as described above) were found to inhibit the proliferative responses of Con A stimulated human peripheral blood lymphocytes.

TABLE II

| | 3H-Thymidine Incorporation (CPM ± SE) | | |
|---|---|---|---|
| No protein | 102,353 ± 5,566 | 91,502 ± 4,333 | 99,700 ± 4,464 |
| 100 μg/mL Human Albumin | 89,860 ± 5,800 | 82,924 ± 11,085 | 94,123 ± 1,633 |
| 100 μg/mL rHuAFP-E. coli | 33,641 ± 3,893 | — | — |
| 100 μg/mL rHuAFP-Baculovirus | — | 31,331 ± 6,303 | — |
| 100 μg/mL HUAFP Fragment I | — | — | 39,019 ± 161 |

Cloning, Expression, and Purification of HuAFP Using A Baculovirus Expression System Recombinant baculovirus expressing HuAFP (or a fragment or analog therof) is constructed according to standard methods known in the art (see, e.g., U.S. Pat. No. 4,745,051). This process generally involves two steps. The gene to be expressed, e.g., rHuAFP or a fragment or analog thereof (described infra), is first cloned into a plasmid transfer vector downstream from a baculovirus promoter that is flanked by baculovirus DNA derived from a nonessential locus, e.g., the polyhedrin gene. This plasmid is then introduced into insect cells along with circular wild-type genomic DNA for homologous recombination to occur. Resulting recombinant progeny are then screened, e.g., using sequential plaque assays to purify recombinant virus away from the nonrecombinant parental strain. Viral amplification is also generally necessary to obtain sufficient virus for protein expression. Recombinant virus are plaque purified and their DNA structure confirmed using standard methods well known in the art.

The rHuAFP cDNA fragment was isolated from plasmid pI18 with EcoRI/BamHI and purified using Geneclean as described infra. The cloning and expression of the HuAFP cDNA in baculovirus was performed using plasmid pVT-PLacZ. Human AFP cDNA was cloned into plasmid pVT-PlacZ (FIG. 7) in frame with the 3'-end of the insect derived melittin signal peptide sequence. The baculovirus vector pVT-PlacZ was modified by replacing the multiple cloning site with the oligonucleotide 5'-GATCTAGAATTCGGATCCGGT-3' (SEQ ID NO: 20) and its complementary fragment, containing EcoRI and BamHI restriction sites in the 5' and 3' direction, reducing the number of non-AFP coding nucleotides between the melittin signal peptide cleavage site and the location of the AFP cDNA insert at the EcoRI endonuclease sequence. The insert was then ligated into the modified pVT-PLacZ vectors at the EcoRI and BamHI DNA sequences.

The generation of recombinant baculovirus containing rHuAFP coding sequences was performed according to standard techniques. Accordingly, purified recombinant baculovirus containing the coding sequences of HuAFP were generated by co-transfection of the pVT-PLacZ transfer vectors and wild-type baculovirus, followed by two rounds of plaque purification. Sf9 insect cells seeded at a density of $1 \times 10^6$ cells/ml in 500 ml spinner flasks were infected with recombinant baculovirus in serum-free Grace medium at a multiplicity of infection of 5. The supernatant containing secreted rHuAFP was harvested and cells were removed by centrifuging at 200× g. The rHuAFP containing medium was concentrated 10–20 fold by ultrafiltration with a YM30 Amicon membrane, dialysed overnight against PBS and then applied to a Con A lectin column (Pharmacia). Bound rHuAFP was eluted with 0.4M methyl α-D mannopyranoside and was purified by elution from Mono Q resin during a linear gradient from 0–100% 1M NaCl in 20 mM phosphate buffer, pH 8.0. Recombinant HuAFP was characterized according to methods well known in the art.

I found that baculovirus produced rHuAFP represented approximately 20% of the total proteins secreted into serum-free medium by the Sf9 insect cells. This AFP was also found to be monomeric as analyzed by non-reducing alkaline PAGE. The majority of the baculovirus- derived HuAFP bound to immobilized Con A. This resulted in effective removal of more than 90% of contaminating proteins which were nonadhered to lectin columns. Final purification of the baculovirus derived rAFP preparations was accomplished by eluting protein with 270–310 mM NaCl from MonoQ beads, yielding a single polypeptide with an apparent molecular mass of approximately 68 kD. We obtained at least 1 mg of purified protein was obtained per liter of growth culture.

The baculovirus-derived rHuAFP molecular weight is similar to the natural human molecule (FIG. 4B). This finding, in addition to the binding of baculovirus-derived rHuAFP and the observed non-adherence of *E. coli*-derived rHuAFP to the ConA column, indicates that the baculovirus-derived rHuAFP is glycosylated. However, the degree of glycosylation of the BrAFP is expected to be less than that of the native molecule, since Sf9 cells infected with recombinant baculovirus have been documented to be deficient in their ability to carry out complex glycosylation normally observed with higher eukaryotic derived proteins. Purity of the isolated baculovirus-derived rHuAFP was verified as a single band on APAGE and SDS-PAGE (FIGS. 4A & 4B), and as a sole peak on FPLC and HPLC chromatograms as shown in FIGS. 4C and 4D, respectively. N-terminal sequencing further confirmed the identity of pure rHuAFP. The N-terminal sequence of the rHuAFP was as follows: Asp-Leu-Glu-Phe-Met-Thr-Leu-His-Arg-Asn (SEQ ID NO: 21). Western blot analysis of serum free supernatants from recombinant baculovirus infected Sf9 cells detected a single immunoreactive band with monospecific anti-HuAFP Ab that was absent form the supernatant of uninfected or wild-type virus-infected Sf9 cells.

Experiments were performed to evaluate the biological activity of the baculovirus produced HuAFP according to methods known in the art. For example, the immunosuppressive activity of 100 g/ml of baculovirus-produced HuAFP was assessed by its ability to suppress human AMLR as described above. As shown in FIGS. 5 and 6A, baculovirus-derived rHuAFP inhibited the proliferative response of autoreactive lymphocytes stimulated by autologous non-T cells at 144 hours. The addition of an identical amount of human serum albumin failed to diminish lymphoproliferative responses.

To demonstrate that rHuAFP was the substrate resposnsible for the inhibition of autoproliferating T cells, blocking of the rHuAFP-mediated suppression of the AMLR was performed using commercial murine anti-human APP monoclonal antibodies (MAb). As shown in FIG. 5, suppression of proliferating autoreactive T cells by 100 μg/ml *E. coli*- and baculovirus-derived rHuAFP was completely blocked by anti-HuAFP MAb. The addition of 100 μg/ml of HSA did not diminish the AMLR response and the presence of MAb alone in the reaction culture was without any effect.

In addition, we tested the biological activity of rHuAFP to suppress the mitogen induced proliferation of peripheral blood lymphocytes (PBL) in RPMI tissue culture media supplemented only with 2 mg/ml purified human albumin (ICN, Mississauga, ON). As shown in Table II and FIG. 6B, suppression of ConA stimulated PBLs occurred with 100 μg/ml rHuAFP whereas the same concentration of albumin was ineffective.

Other rHuAFPs (e.g., rHuAFP (Amino acids 1(Thr)—590 (Val); SEQ ID NO: 4); Domain I (Amino acids 1(Thr)—197 (Ser), SEQ ID NO: 6; Domain II (Amino acids 198 (Ser)—389 (Ser), SEQ ID NO: 7); Domain III (Amino acids 390 (Gln)—590 (Val), SEQ ID NO: 8); Domain I+II (Amino acids 1 (Thr)—389 (Ser), SEQ ID NO: 9); Domain II+III, (Amino acids 198 (Ser)—590 (Val), SEQ ID NO: 10); rHuAFP Fragment I (Amino acids 266 (Met)—590 (Val), SEQ ID NO: 11) can be produced using the above described baculovirus expression system according to standard methods, e.g., any of the methods described herein.

In one working example, the vector pVT-PLacZ/HuAFP (amino acids 1–590) is constructed by inserting the cDNA for HuAFP into pVT-P10, an intermediate vector in the construction of pVT-PLacZ (Richardson et al., (1992) Engineering Glycoproteins for secretion using the baculovirus expression system. In: Baculovirus and Recombinant Protein Production Processes, eds., J. M. Viak, E.-J. Schlaeger, and A. R. Bernard, Editiones Roche, Basel, Switzerland. pp. 67–73.). The pVT-P10 vector is digested with BamHI, followed by incubation with mung bean Nuclease (New England Biolabs, Mississauga, Ont.). The vector is then further hydrolyzed with EcoRl downstream of the blunt-end BamHl site to facilitate directional cloning of the HuAFP cDNA. The rHuAFP cDNA encoding amino acids 1–590 is obtained by PCR amplification, employing the following oligonucleotide primers: (5'-AAAAAACTCGAGATACACTGCATAGAAATGAA-3'; SEQ ID NO: 22), containing an XhoI site and (5'-AAAAAAGAATTCTTAAACTCCCAAAGCAGCACG-3'; SEQ ID NO:23), containing an EcoRl site, and plasmid pl18 as the template DNA containing the coding region of HuAFP. The PCR reaction is performed according to standard methods, e.g., in a reaction mixture containing 34 μL H$_2$O, 10 μL 10× reaction buffer, 20 μL dNTP, 2 μL DNA template, 10 μL 10 pmol/μL 5' primer, 10 μL 10 pmol/μL 3' primer, 1 μL glycerol, 10 μL DMSO, and 1 μL Pfu polymerase. Annealing, extension, and denaturation temperatures are also performed according to standard contions, e.g., 50° C., 72° C., and 94° C., respectively, for 30 cycles, using the GeneAmp PCR System 9600 (Perking Elmer Cetus). DNA from the PCR reaction is purified using the Genaclean kit (Bio 11 Inc., LaJolla, Calif.). The rHuAFP cDNA fragment is first digested with XhoI followed by treatment with mung bean nuclease. Next, the HuAFP cDNA is digested with EcoRl to facilitate directional cloning into pVT-p10. The PCR-produced rHuAFP cDNA is ligated into the blunt ended 5' BamHl site and into the 3' EcoRl site. The β-galactosidase gene containing at the 3' end a polyadenylation site from SV40, isolated from the vector pJV-Nhe1 (Vialard et al., (1990) Synthesis of the membrane fusion and hemagglutinin proteins of Measles Virus, using a novel baculovirus vector containing the βgalactosidase gene, J. Virology 64: 37–50) by using the restriction enzyme BamHl, is then inserted into the compatible BglII, producing the final construct: pVT-PLacZ/HuAFP (containing amino acids 1–590). Such a construct is then used for expressing rHuAFP (amino acids 1–590).

Use

Recombinant HuAFP (or fragments and analogs thereof) produced using the expression systems described herein are useful for diagnostic and therapeutic uses.

Recombinant HuAFP (or fragments and analogs thereof) can be administered to a mammal, e.g., a human patient, in an effective amount either alone or in combination with a pharmaceutically acceptable carrier or diluent. Generally, a dosage of 0.1 ng/kg to 10 g/kg body weight is adequate. Suitable carriers and their formulation are described for example in Remington's *Pharmaceutical Sciences* by E. W. Martin. The amount of rHuAFP (or a fragment or analog thereof) to be administered will vary depending upon the manner of administration, the age and body weight of the patient, and with the type of disease, and size of the patient predisposed to or suffering from the disease. Preferable routes of administration include, for example, oral, subcutaneous, intravenous, intraperitoneally, intramuscular, transdermal or intradermal injections which provide continuous, sustained levels of the drug in the patient. In other preferred routes of administration, such rHuAFP can be given to a patient by injection or implantation of a slow release preparation, for example, in a slowly dissociating polymeric or crystalline form; this type of sustained administration can, if desired, follow an initial delivery of the drug by more conventional routes (for example, those described above). Alternatively, such rHuAFP can be administered using an external or implantable infusion pump, thus allowing a precise degree of control over the rate of drug release, or through installation of the drug in the nasal passages in a fashion similar to that used to promote absorption of insulin. As an alternative to nasal transmucosal absorption, such rHuAFP can be delivered by aerosol deposition of a powder or solution into the lungs.

Autoimmune Diseases

The rHuAFP molecules of the invention provide compositions for therapies useful in the prevention and treatment of autoimmune diseases. In general, autoimmune diseases are characterized by a loss of tolerance to self antigens, causing cells of the immune systems, e.g., T or B cells (or both), to react against self tissue antigens. Autoimmune diseases may involve any organ system, although some are affected more commonly than others. Examples of tissues affected by autoimmune conditions include: the white matter of the brain and spinal cord in multiple sclerosis; the lining of the joints in rheumatoid arthritis; and the insulin secreting β islet cells of the pancreas in insulin-dependent diabetes mellitus. Other forms of autoimmune disease destroy the connections between nerve and muscle in myasthenia gravis or destroy the kidneys and other organs in systemic lupus erythematosus. Examples of other autoimmune diseases include, without limitation, Addison's disease, Crohn's disease, Graves' disease, psoriasis, scleroderma, and ulcerative colitis.

The art provides a wide variety of experimental animal systems, transgenic and non-transgenic, for testing therapies for human illness involving autoimmune diseases (see e.g., Paul, W. E., *Fundamental Immunology*, 2nd ed., Raven Press, New York, 1989; Kandel et al. *Principles of Neural Science*, 3rd ed., Appleton and Lange, Norwalk, Conn., 1991; and *Current Protocols In Immunology*, Coligan, J. E., Kruisbeek, A. M., Margulies, D. H., Shevach, E. M., and Strober, eds., Green Publishing Associates (John Wiley & Sons), New York, 1992); and U.S. Ser. No. 08/377,309. Based on the above-described experimental results showing immunosuppressive activity of rHuAFP (or fragments or analogs thereof), it is reasonable to believe that any number of autoimmune diseases can be treated by administration of such rHuAFP produced in any of the expression systems described herein. Accordingly, the invention provides for the use of rHuAFP (or a fragment or analog thereof) for treatment (i.e., prevention or suppression or amelioration or promotion of remission) of an autoimmune disease. Animal systems useful for evaluating the efficacy of such rHuAFP or an immune cell anti-proliferative fragment or analog thereof in treating autoimmune diseases can be evaluated using any of the methods described in U.S. Ser. No. 08/377,309.

Diagnosis and Treatment of Cancer

The rHuAFP compounds of the invention provide compositions for diagnostic methods and therapies useful for the prevention and treatment of neoplasms.

Recombinant rHuAFP (a fragment or analog thereof), for example, can be attached to a detectable label to produce an agent useful for detecting and localizing a neoplasm in vivo, in situ, or in vitro . Methods for attaching such labels to proteins are known in the art. For example, rHuAFP (or a fragment or analog thereof) is bound to radioisotopes suitable for in vivo imaging, such as $^{99m}$Tc, $^{131}$I, or $^{111}$In. Those skilled in the art will understand that there are numerous well known techniques for generating such radioisotopes and binding such radioisotopes to rHuAFP (or a fragment or analog thereof).

Those skilled in the art will also understand that the imaging agent(s) described above are administered by various well known techniques, for example, by injection at a specific site or by intravenous infusion. Readings are taken by standard techniques such as a body scanning scintigram using a gamma camera interfaced with a computer. See, e.g., U.S. Ser. No. 08/377,311.

Recombinant HuAFP (or an anti-neoplasm fragment or analog thereof) is also useful for inhibiting the growth of a neoplasm, e.g., breast or prostate carcinomas. Such rHuAFP is also useful for protecting a mammal from developing a neoplasm. Those skilled in the art will understand that any number of methods, both in vitro and in vivo, are used to determine the efficacy of rHuAFP (or a anti-neoplasm fragment or analog thereof) as an anti-neoplasmic agent. For example, the reduction of tumor growth can be monitored in a mouse or rat growing a prostate cancer (e.g., tumor xenografts of LNCaP androgen receptor-positive human prostate cancer cell line) following the administration of the test compound. See, e.g., the methods disclosed in U.S. Ser. No. 08/377,311.

Furthermore, if desired, rHuAFP (or a fragment or analog thereof) can be coupled to a cytotoxic agent such as diphtheria toxin, Pseudomonas exotoxin A; ricin and other plant toxins such as abrin, modeccin, volkensin, viscumin; chlorea toxin (produced by *Vibrio cholerae* bacteria); the so-called "Shiga-like" toxins (produced by *E. coli* and other enteric bacteria); Salmonella heat-labile enterotoxin; and *E. coli* heat-labile enterotoxin. Those skilled in the art will further realize that there are numerous radioisotopes or chemocytotoxic agents that can be coupled to rHuAFP (or a fragment or analog thereof), and delivered to specifically destroy, inactivate or inhibit a tumor. Examples of such cytotoxic agents include, without limitation, anti-cancer agents such as doxorubicin, as well as α-emitting radionuclides such as astatine and β-emitting nuclides such as yttrium. Experimental systems are well known for evaluating the efficacy of such hybrid cytotoxic agents.

Proliferative Agents

Recombinant HuAFP (or a cell-stimulating fragment or analog thereof) is also useful for promoting cell proliferation, e.g., proliferation of bone marrow cells, and for the prevention of side effects of immunosuppressive therapy, radiotherapy or chemotherapy, or other therapies known to depress the immune system and suppress bone marrow production, causing myelotoxicity. Accordingly, rHuAFP (or a fragment or analog thereof) is employed to treat deficiencies in hematopoietic progenitor or stem cells, or related disorders. Such rHuAFP may also be employed in methods for treating cancer and other pathological states resulting in myelotoxcity, e.g., exposure to radiation or drugs, and including for example, leukopenia, bacterial and viral infections, anemia, B cell or T cell deficiencies, including immune cell or hematopoietic cell deficiency following autologous or non-autologous bone marrow transplantation. Such rHuAFP is also useful to stimulate development of megakaryocytes and natural killer cells in vitro or in vivo.

Media and compositions containing rHuAFP of the invention are also useful for treating cancers that are treated by bone marrow transplants (BMT) that involve removing bone marrow cells from the patient, maintaining these cells in an ex vivo culture while the patient is treated with radiation or chemotherapy, and then transplanting these cells back into the patient after the treatment has been completed to restore the patient's bone marrow. Accordingly, rHuAFP of the invention may be employed for BMT as a means for reconstituting bone marrow in ex vivo cell culture medium and for promoting bone marrow cell proliferation in vivo. Such rHuAFP is also useful for other cell therapies, e.g. cell expansion and/or gene therapy protocols, and for therapies requiring ex vivo cell culture. Recombinant HuAFP of the invention is also useful in the prevention of autologous or allogenic bone marrow transplant rejection.

Culture Media

The invention further provides a media containing rHuAFP (or a cell-stimulating fragment or analog thereof) for cell culture. While the media of the invention generally does not require the use of serum (e.g., fetal bovine serum, calf serum, horse serum, normal mouse serum, human serum, porcine serum, rabbit serum etc.), since such rHuAFP is intended to replace or supplement the use of serum, those skilled in the art will understand and recognize that serum can be added if desired. Media formulations are generally prepared according to methods known in the art. Accordingly, any standard medium, e.g., RMPI-1630 Medium, CMRL Medium, Dulbecco's Modified Eagle Medium (D-MEM), Fischer's Medium, Iscove's Modified Dulbecco's Medium, McCoy's Medium, Minimum Essential Medium, NCTC Medium, and the like can be formulated with rHuAFP (or a fragment or analog thereof) at the desired effective concentration. If desired, media supplements, e.g., salt solutions (e.g., Hank's Balanced Salt Solution or Earle's Balanced Salt Solution), antibiotics, nucleic acids, amino acids, carbohydrates, and vitamins are added according to known methods. If desired, growth factors, colony-stimulating factors, cytokines and the like can also be added to media according to standard methods. For example, media of the invention can contain any of the following substances, alone or in combination, with rHuAFP (or a fragment or analog thereof): erythropoietin, granulocyte/macrophage colony-stimulating factor (GM-CSF), granulocyte colony-stimulating factor (G-CSF), macrophage colony-stimulating factor (M-CSF), an interleukin (e.g., IL-1, IL-2, IL-3, IL-4, IL-5, etc.), insulin-growth factor (IGF), transferrin, albumin, and stem-cell growth factor (SCF). Media of the invention are useful for culturing a variety of eukaryotic cells, e.g., mammalian cells, yeast cells, amphibian cells, and insect cells. Media of the invention can also be used for culturing any tissue or organ. Furthermore, such media can be used in a variety of culture conditions and for a variety of biological applications. Examples of such culture conditions include, without limitation, bioreactors (e.g., continuous or hollow fiber bioreactors), cell-suspension cultures, semisolid cultures, liquid cultures, and long-term cell suspension cultures. Media of the invention are also useful for industrial applications, e.g., culturing hybridoma cells, genetically-engineered mammalian cells, tissues or organs.

All publications, manufacturer's instructions, patents, and patent applications mentioned in this specification are herein incorporated by reference to the same extent as if each individual publication or patent application was specifically and individually indicated to be incorporated by reference.

I claim:

1. Substantially pure biologically-active recombinant human alpha-fetoprotein which is unfused to additional amino acids, wherein said recombinant human alpha-fetoprotein comprises an amino acid sequence which is at least 90% homologous to amino acids 1 to 590 shown in FIG. 1 (SEQ ID NO: 5).

2. The pure recombinant human alpha-fetoprotein of claim 1, wherein the amino acid sequence of said human alpha-fetoprotein consists of amino acids 1 to 590 shown in FIG. 1 (SEQ ID NO: 5).

3. Substantially pure biologically-active recombinant human alpha-fetoprotein which is unfused to additional amino acids, comprising a sequence substantially the same as amino acids 1 to 389 shown in FIG. 1 (SEQ ID NO: 9).

4. The pure recombinant human alpha-fetoprotein of claim 3, wherein said human alpha-fetoprotein is produced using a prokaryotic cell.

5. Substantially pure biologically-active recombinant human alpha-fetoprotein which is a fragment of human alpha-fetoprotein, wherein said fragment comprises an amino acid sequence which is at least 90% homologous to amino acids 198 to 590 shown in FIG. 1 (SEQ ID NO: 10).

6. The pure recombinant human alpha-fetoprotein of claim 5, wherein said human alpha-fetoprotein is produced using a prokaryotic cell.

7. Substantially pure biologically-active recombinant human alpha-fetoprotein which is a fragment of human alpha-fetoprotein, wherein said fragment comprises amino acids 198 to 389 shown in FIG. 1 (SEQ ID NO: 7).

8. The pure recombinant human alpha-fetoprotein of claim 7, wherein said human alpha-fetoprotein is produced using a prokaryotic cell.

9. Substantially pure biologically-active recombinant human alpha-fetoprotein which is a fragment of human alpha-fetoprotein, wherein said fragment comprises an amino acid sequence which is at least 90% homologous to amino acids 390 to 590 shown in FIG. 1 (SEQ ID NO: 8).

10. The pure recombinant human alpha-fetoprotein of claim 9, wherein said human alpha-fetoprotein is produced using a prokaryotic cell.

11. Substantially pure biologically-active recombinant human alpha-fetoprotein which is a fragment of human alpha-fetoprotein, wherein said fragment comprises an amino acid sequence which is at least 90% homologous to amino acids 267 to 590 of FIG. 1 (SEQ ID NO:12).

12. The pure recombinant human alpha-fetoprotein of claim 11, wherein said human alpha-fetoprotein is produced using a prokaryotic cell.

13. A therapeutic composition comprising at least one of the substantially pure human recombinant alpha-fetoproteins of claims 1, 3, 5, 7, 9, and 11.

14. The pure recombinant human alpha-fetoprotein of claim 1, wherein said human alpha-fetoprotein is produced using a prokaryotic cell.

15. The pure recombinant human alpha-fetoprotein of claim 3, wherein the amino acid sequence of said human alpha-fetoprotein consists of amino acids 1 to 389 shown in FIG. 1.

16. The pure recombinant human alpha-fetoprotein of claim 5, wherein said fragment of human alpha-fetoprotein consists of amino acids 198 to 590 shown in FIG. 1.

17. The pure recombinant human alpha-fetoprotein of claim 7, wherein said fragment of human alpha-fetoprotein consists of amino acids 198 to 389 shown in FIG. 1.

18. The pure recombinant human alpha-fetoprotein of claim 9, wherein said fragment of human alpha-fetoprotein consists of amino acids 390 to 590 shown in FIG. 1.

19. The pure recombinant human alpha-fetoprotein of claim 11, wherein said fragment of human alpha-fetoprotein consists of amino acids 267 to 590 shown in FIG. 1.

* * * * *